(12) United States Patent
Wang

(10) Patent No.: US 9,855,136 B2
(45) Date of Patent: Jan. 2, 2018

(54) POSTERIOR CHAMBER INTRAOCULAR LENS

(71) Applicant: EYEBRIGHT MEDICAL TECHNOLOGY (BEIJING) CO., LTD., Beijing (CN)

(72) Inventor: Zhao Wang, Beijing (CN)

(73) Assignee: EYEBRIGHT MEDICAL TECHNOLOGY (BEIJING) CO., LTD., Beijing (CN)

( * ) Notice: Subject to any disclaimer, the term of this patent is extended or adjusted under 35 U.S.C. 154(b) by 0 days.

(21) Appl. No.: 14/372,245

(22) PCT Filed: Jan. 18, 2013

(86) PCT No.: PCT/CN2013/000057
§ 371 (c)(1),
(2) Date: Jul. 15, 2014

(87) PCT Pub. No.: WO2013/107288
PCT Pub. Date: Jul. 25, 2013

(65) Prior Publication Data
US 2014/0358225 A1    Dec. 4, 2014

(30) Foreign Application Priority Data

Jan. 19, 2012 (CN) .......................... 2012 1 0017055
Jan. 19, 2012 (CN) .......................... 2012 1 0017070
Sep. 12, 2012 (CN) .......................... 2012 1 0335578

(51) Int. Cl.
*A61F 2/16* (2006.01)
*A61F 2/00* (2006.01)

(52) U.S. Cl.
CPC .............. *A61F 2/1624* (2013.01); *A61F 2/16* (2013.01); *A61F 2/161* (2015.04); *A61F 2/1613* (2013.01);
(Continued)

(58) Field of Classification Search
CPC ..... A61F 2/16; A61F 2002/009; A61F 2/1694
(Continued)

(56) References Cited

U.S. PATENT DOCUMENTS 4,642,114 A    2/1987 Rosa
4,834,750 A    5/1989 Gupta
(Continued)

FOREIGN PATENT DOCUMENTS

CN    1933791       3/2007
CN    101090679     12/2007
(Continued)

OTHER PUBLICATIONS

International Search Report and Written Opinion from PCT/CN2013/000057 dated May 23, 2013.
(Continued)

*Primary Examiner* — David H Willse
*Assistant Examiner* — Javier Blanco
(74) *Attorney, Agent, or Firm* — Calfee, Halter & Griswold LLP

(57) ABSTRACT

The present invention relates to a posterior chamber intraocular lens (IOL), comprising: an optic consisting of an effective optical area and an effective optical area edge; at least two haptics connected to the optic, wherein a posterior surface of the effective optical area is a convex surface, and a basic spherical surface thereof has a radius of curvature in a range of 6.6 mm-80.0 mm. The effective optical area of the posterior chamber IOL adopts a design with the posterior surface obviously convex, which reduces the distance between the posterior surface of the effective optical area of the IOL and the posterior capsule, improves the stability of a spatial position of the IOL in a capsule bag, and reduces an incidence rate of posterior capsule opacification (PCO) after implantation of the IOL; since the effective optical area
(Continued)

anterior surface is relatively flat, the IOL haptics will not be tightly pressed on the effective optical area anterior surface upon folding, the haptics are more easily unfolded after implantation into the eye and the support haptics are not mutually adhered to the effective optical area, and meanwhile the IOL imaging quality can be improved and/or the visual quality of the astigmatism sufferer is enhanced.

4 Claims, 20 Drawing Sheets

(52) U.S. Cl.
CPC ............ *A61F 2/1629* (2013.01); *A61F 2/164* (2015.04); *A61F 2/1618* (2013.01); *A61F 2002/0091* (2015.04)

(58) Field of Classification Search
USPC .............................................. 623/6.16, 6.17
See application file for complete search history.

(56) References Cited

U.S. PATENT DOCUMENTS

| | | | |
|---|---|---|---|
| 5,290,892 | A | 3/1994 | Namdaran et al. |
| 5,814,680 | A | 9/1998 | Imafuku et al. |
| 6,162,249 | A | 12/2000 | Deacon et al. |
| 6,468,306 | B1 | 10/2002 | Paul et al. |
| 2002/0173845 | A1 | 11/2002 | Bandhauer et al. |
| 2003/0018384 | A1 | 1/2003 | Valyunin et al. |
| 2005/0131534 | A1 | 6/2005 | Rozakis et al. |
| 2005/0283234 | A1 | 12/2005 | Zhou et al. |
| 2006/0142855 | A1 | 6/2006 | Vaudant et al. |
| 2008/0013043 | A1 | 1/2008 | Ye et al. |
| 2010/0131059 | A1* | 5/2010 | Callahan ............... A61F 2/1629 623/6.23 |

FOREIGN PATENT DOCUMENTS

| | | |
|---|---|---|
| CN | 101437468 | 5/2009 |
| CN | 2015072212 | 9/2010 |
| CN | 102014793 | 4/2011 |
| CN | 202223385 | 5/2012 |
| CN | 202446298 | 9/2012 |
| CN | 202446299 | 9/2012 |
| CN | 103211664 | 7/2013 |
| EP | 128784 | 12/1984 |
| JP | 2011500189 | 1/2011 |
| WO | 03/009051 | 1/2003 |

OTHER PUBLICATIONS

Buehl,I et al., "Effect of intraocular lens design on posterior capsule opacifaction", J. of Cataract & Refractive Surgery, vol. 34, issue 11, pp. 1976-1985, Nov. 2008.
Office Communication from European Application No. 13738119.0 dated Aug. 31, 2015.
Office action from Chinese Application No. 201210335578.3 dated Apr. 3, 2015.
Office action from Chinese Application No. 201210017070.9 dated Mar. 18, 2015.
Office action from Japanese Application No. 2014-552488 dated May 10, 2016.
Office action from Chinese Application No. 201210335578.3 dated Nov. 27, 2015.
Office action from Chinese Application No. 201210017070.9 dated Oct. 22, 2014.
Office action from Chinese Application No. 201210017055.4 dated Oct. 24, 2014.
"Design of aspheric FFA camera based on eye model", Wang Zhao-qi et al. Optics and Precision Engineering, Jul. 2010, 9 pgs. English abstract attached.
Office action from Chinese Application No. 201210017070.9 dated Aug. 14, 2015.
Office Action from Japan Application No. 2014552488 dated Jan. 17, 2017.

* cited by examiner

POSTERIOR CHAMBER INTRAOCULAR LENS

CROSS REFERENCE TO RELATED APPLICATIONS

The present application is the U.S. national phase entry of PCT/CN2013/000057, with an international filing date of Jan. 18, 2013, which claims the benefit of Chinese Patent Application Nos. 201210017070.9, filed Jan. 19, 2012; 201210017055.4, filed Jan. 19, 2012 and 201210335578.3 filed Sep. 12, 2012, the entire disclosures of which are incorporated herein by reference.

FIELD OF THE INVENTION

The present invention mainly relates to a posterior chamber intraocular lens. Specifically, the present invention relates to a posterior chamber intraocular lens with an obviously convex effective optical area posterior surface (the effective optical area obviously protruding rearward), which can improve the stability of spatial position of the intraocular lens in a capsule bag and facilitate reduction of an incidence rate of Posterior Capsule Opacification (PCO) after the implantation of the intraocular lens. In particular, the present invention relates to a posterior chamber intraocular lens with an obviously convex effective optical area posterior surface, which can improve the stability of spatial position of the intraocular lens in a capsule bag, facilitate reduction of an incidence rate of secondary cataract (PCO) after the implantation of the intraocular lens, and improve imaging quality of the intraocular lens and/or improve visual quality of an astigmatism sufferer.

BACKGROUND OF THE INVENTION

An intraocular lens (IOL) is an artificial lens which is used for implantation into a human eye to replace a natural lens in the human eye which becomes opacified due to the cataract disease, or which is used in a refractive operation to correct vision of the human eye. An intraocular lens usually consists of a circular optic and support haptics disposed on the circumference thereof. The optic of the intraocular lens is directly connected to the support haptics. The optic of the intraocular lens consists of an effective optical area (also called as "the optic body" in the art) and an effective optical area edge. The intraocular lens made of a soft material is often called a foldable intraocular lens and may be folded or rolled to get smaller and then be implanted into a human eye through a smaller incision (from less than 2 mm to 3 mm). The folded or rolled intraocular lens can unfold automatically after entry into the eye.

The flexible foldable intraocular lenses are generally classified into one-piece type and three-piece type according to the engagement manner of the optic and the haptics. In the one-piece type flexible foldable intraocular lens, the optic and the support haptics are integral and made of the same piece of soft material. In the three-piece type flexible foldable intraocular lens, the optic and the support haptics are processed separately and then combined and connected together.

So far, the soft materials for preparing the foldable intraocular lens are generally classified into silicone, hydrophilic acrylate (hydrogel), hydrophobic acrylate, and polymethyl methacrylate (PMMA). The hydrophobic acrylate is currently the most widely used IOL material. It has the advantages such as a high refractive index and a moderate unfolding speed from a folded state. For example, the U.S. Pat. Nos. 4,834,750, 5,290,892 and 5,814,680 disclose several different methods for preparing the IOL from hydrophobic acrylate materials.

The posterior chamber IOL 1 (hereinafter referred to as "IOL") maintains at a relative position in a posterior chamber capsule bag 12 by means of the interaction force between the support hapics 5 and the capsule bag 12 after being implanted into a human eye. The retraction and expansion of the capsule bag act upon the support haptics, so that the IOL connected to the haptics is pressed or stretched to move forward and rearward along an ocular axis direction D-D'. The optics 2 of the IOL 1 and a cornea 11 of the human eye jointly form a dioptric system and bear about 30% of the refractive power of the human eye, as shown in FIG. 1. In this note, when light enters from a substance into another substance with different optical density, propagation direction of the light will deflect. This phenomenon is called refraction phenomenon. Diopter indicates a magnitude of the refraction phenomenon (refractive power), with a measure unit of diopter ("D" in short). 1D refractive power is equivalent to focusing parallel light rays on a 1-meter focal length. The action of the eye refracting light rays is called refraction. Focal power of light is used to represent capability of refraction, and is also called diopter. The diopter is the lens's refraction intensity for the light rays. The diopter is a measure unit of refractive power and represented as D. When parallel light rays pass through the refraction substance, and the refractive power of the refraction substance at the 1-meter focusing point is 1 diopter or 1D. As for a lens, the diopter refers to the measure unit of a focal power of the lens, e.g., when a focal length of a lens is 1M, the refractive power of the lens is 1D diopter, inversely proportional to the focal length. The refractive power of the lens is $F=1/f$, wherein f is the focal length of the lens. In the equation, the measure unit of the refractive power is diopter with a symbol of D, a dimension of $L^{-1}$, $1D=1\ m^{-1}$.

Those skilled in the art appreciate that imaging quality of the IOL is a factor that must be considered during design of an IOL product.

The IOL, in addition to providing the refractive power to compensate the refractive power of the cornea, needs to correct the cornea and its own various high order aberrations to achieve high-quality imaging quality.

Refractive error is a factor substantially affecting the imaging quality, wherein astigmatism is a common refractive error phenomenon of human eyes and refers to a phenomenon that the eyeball has inconsistent refractive power on different meridian lines, or unequal diopters on the same meridian line, so that parallel light rays entering the eye cannot form a focal point on a retina, but instead form a focal line. Astigmatism is clinically classified into regular astigmatism and irregular astigmatism. The regular astigmatism means that two meridian lines with a maximum refractive power difference are called main meridian lines, and the two main meridian lines are perpendicular to each other. The irregular astigmatism means that astigmatism bending degrees of meridian lines are inconsistent. The regular astigmatism may be corrected through lens.

Among normal population, those whose cornea astigmatism is greater than 1.5D accounts for 15%-29%, which seriously affects people's visual quality. The newest treatment method for cataract with astigmatism is to implant an astigmatism IOL (Toric IOL) in the eye to achieve normal refraction and meanwhile correct cornea astigmatism.

Toric IOL was marketed since 1997 and consecutively ratified by FDA of the United States and the security certification of European Community (EC). The earliest Toric IOL is achieved by attaching a cylindrical surface to the posterior surface of the IOL (the basic surface shape is convex in the front and flat in the rear; the cylindrical surface is directly attached to the posterior surface). Currently a relatively mature Toric IOL adopts a design of a toric surface, which integrates cylindrical surface refraction effect with a spherical surface and an aspherical surface. Typically, Wherein:

$$A = \frac{n+2}{n}\varphi\rho_1^2 - \left(\frac{2n+1}{n-1}\varphi^2 + \frac{4n+4}{n}\varphi\sigma_1\right)\rho_1 + \frac{3n+1}{n-1}\varphi^2\sigma_1 + \frac{3n+2}{n}\varphi\sigma_1^2 + \frac{n^2}{(n-1)^2}\varphi^3 \quad (3)$$

TABLE 1 radii of curvature of the two surfaces with different refractive indices when the IOL spherical aberration is minimum

| materials | Refractive index | Radius of curvature | 30D | 25D | 20D | 15D | 10D | 5D |
| --- | --- | --- | --- | --- | --- | --- | --- | --- |
| silicone/ hydrophilic acrylate | n = 1.46 | $r_1$(mm) | 5.64 | 6.56 | 8.21 | 10.85 | 16.26 | 31.97 |
|  |  | $r_2$(mm) | 26.90 | 31.40 | 39.49 | 51.83 | 78.35 | 154.89 |
| hydrophobic acrylate | n = 1.55 | $r_1$(mm) | 8.08 | 9.70 | 12.12 | 16.16 | 24.24 | 48.49 |
|  |  | $r_2$(mm) | 60.73 | 72.90 | 91.16 | 121.58 | 182.43 | 365.00 |

Acrys of astigmatism IOL produced by Alcon Corporation of the United States adopts Toric design at the posterior surface of the lens and can correct 1.03D-4.11D astigmatism of human eye cornea; TECNIS Toric series IOL produced by AMO Inc. may correct 0.69D-2.74D astigmatism of human eye cornea. Meanwhile, the improved "L" haptics or "C" haptics are used to improve stability of the lens in the human eye.

Besides, high order aberrations also affect the imaging quality. The high order aberrations mainly comprise spherical aberration and comatic aberration.

In a human eye dioptric system, the spherical aberration is a factor that most affects the imaging quality besides refractive error, and appears particularly obvious when the human eye is in a dim condition with a large pupil (the pupil diameter 4.5 mm-6.0 mm). A radius of curvature of an optical surface with a minimum IOL spherical aberration may be obtained by calculation, and the obtained radius of curvature of the optical surface is related to the refractive index of the IOL material. Table 1 shows radii of curvature of the two surfaces with different refractive indices when the effective optical area is a spherical surface design and when the IOL spherical aberration is minimum. The following equations are used upon calculation:

$$\frac{r_2}{r_1} = \frac{n(2n+1)}{2n^2 - n - 4} \quad (1)$$

$$\varphi = \varphi_1 + \varphi_2 = \frac{n-n'}{r_1} + \frac{n'-n}{r_2} = (n-n')\cdot\left(\frac{1}{r_1} - \frac{1}{r_2}\right) \quad (2)$$

$r_1$ and $r_2$ are respectively radii of curvature of the IOL anterior and posterior surfaces, n is the refractive index of IOL material, n' is the refractive index of vitreous body and aqueous humor, and $\varphi_1$ and $\varphi_2$ are diopters of the anterior and posterior surfaces. Equation (1) is derived as follows when the spherical aberration equation of the lens achieves an extreme value.

$$\delta L_0' = -\frac{1}{2n'u'^2}h^4 A$$

The spherical aberration of an IOL with a given refractive power and a given refractive index changes in a parabolic form, as shown in FIG. 2. In the graph shown in FIG. 2, the horizontal ordinate $\rho_1$ represents a reciprocal of a radius of curvature of IOL effective optical area anterior surface (the smaller $\rho_1$ is, the flatter the effective optical area anterior surface is), and $\rho_1$ with different magnitudes substantially correspond to the prior-art IOL with different surface shape designs; the longitudinal ordinate $\delta L_0'$ represents a magnitude of spherical aberration. As can be seen from FIG. 2 and Table 1, the surface shape of the IOL effective optical area 3 will substantially affects the imaging quality. To minimize the spherical aberration ($\delta L_0'$) to improve the imaging quality, the surface shape of the prior-art spherical IOL is generally convex-flat (i.e. convex in the front and flat in the rear) or double-convex (the effective optical area anterior surface is obviously convex and the effective optical area posterior surface is slightly rearwardly convex), conforming to the surface shape design principle of minimizing the primary spherical aberration in a wholly curving manner in optical design. The types of the radii of curvature of the prior-art IOL anterior and posterior surfaces are approximate to what are shown in Table 1: the posterior surface tends to be flat and the anterior surface is obviously convex, and the anterior surface radius of curvature is universally smaller than the curvature radius of the posterior surface. Clinical implantation results indicate that the convex-flat or obviously forwardly convex effective optical area structure of the spherical IOL achieves a better imaging quality. Therefore, many IOLs choose to adopt these two common surface shape designs so far.

Regarding the case in which the radius of curvature of the effective optical area posterior surface is obviously smaller than that of the effective optical area anterior surface, the IOL with an obviously rearwardly convex effective optical area, upon application, generates a larger residual spherical aberration than the so far universally-used ordinary IOL with flat-convex or slightly rearwardly convex surface shape as mentioned above. As shown in FIG. 2, the design with a small radius of curvature of the IOL effective optical area posterior surface sacrifices part of imaging quality because the difference of radii of curvature of the effective optical area anterior and posterior surfaces makes the obviously rearwardly convex IOL itself have a larger residual spherical aberration. The larger the residual spherical aberration is, the poorer the imaging quality is.

Besides, those skilled in the art should also appreciate that although the prior-art IOL adopting ordinary aspherical (namely, a single aspherical coefficient Q value) surface shape design can compensate spherical aberration, the IOL implanted into the posterior chamber is not always in a perfect central position of human eye posterior chamber, and gets tilted or off-center to some degree and thereby generates the other higher order aberrations besides spherical aberration, typically the comatic aberration. The imaging quality of the prior-art IOL will be reduced due to an error of actual position of the IOL in the eye, and optical performance is extremely sensitive to actual clinical situations.

Posterior Capsule Opacification, the so-called secondary cataract, is a common complication after implantation of the IOL. Posterior capsule opacification is caused by multiplication and migration of the residual lens epithelial cells after cataract surgery to the place between the IOL posterior surface and posterior capsule. The effective optical area of the IOL adopts a sharp right-angle edge design, for example, in U.S. Pat. Nos. 6,162,249 and 6,468,306, which has already been proved a method of effectively reducing posterior capsule opacification because this design can prevent the lens epithelial cells from migrating to the place between the IOL posterior surface and posterior capsule (see the article by Buehl et. al., Journal of Cataract and Refractive Surgery, vol. 34, pages 1976-1985). This sharp right-angle edge design can be implemented on the three-piece IOL more easily because the support haptics are very thin and they are inserted onto the effective optical area. It is more difficult to implement this sharp right-angle edge design on the one-piece IOL because the support haptics are integrally connected with the effective optical area and the support haptics are made of a soft material and need to be produced wider and thicker. To implement the sharp right-angle edge design on the one-piece IOL, the effective optical area needs to have a thick edge and thin support haptics, or the right-angle edge step has a small fall. If the edge of the effective optical area is too thick, an overall size of the IOL will be increased and a small-incision surgery will be made more difficult; if the support haptics are too thin, the action force between it and the capsule is insufficient and the IOL is unstable in the capsule; if the right-angle edge step has a too small fall, it cannot play a role of preventing the migration of the lens epithelial cells.

In an optical design of the prior-art posterior chamber IOL, in order to reduce the spherical aberration and improve the imaging quality, a spherical IOL is generally designed to have an obviously convex anterior surface and a relatively flat posterior surface, with a radius of curvature of the anterior surface being universally smaller than that of the posterior surface. Aspherical IOLs for correcting the spherical aberration and Toric IOL for correcting astigmatism developed subsequently both conform to this design concept. The effective optical area of the prior-art IOL is not rearwardly convex obviously (even in a planar shape), thus a larger gap is left between the IOL posterior surface and the posterior capsule after the implantation of the IOL into the human eye, which causes the position of the IOL unstable and causes posterior capsule opacification after the surgery. Even if the IOL adopts the right-angle edge design (square edge design), when the human eye's ciliary muscle automatically adjusts by retracting or expanding as the eye views far or near, the posterior capsule is driven to move forward and backward under pressure of the vitreous humor, pressure and uneven traction applied by the root area of the IOL support haptics to the posterior capsule bring PCO into the effective optical area edge of the IOL through the flow of the vitreous humor.

At present, secondary cataract has already become a problem that troubles the cataract sufferer and is to be solved urgently. In order to improve stability of a spatial position of the intraocular lens in a capsule bag and to facilitate reduction of an incidence rate of secondary cataract after implantation of the intraocular lens, if the prior-art IOL effective optical area posterior surface adopts a small radius of curvature, it will certainly sacrifice part of imaging quality of the prior-art IOL.

To those skilled in the art, a good IOL design should consider and balance the following factors: to ensure the stability of the IOL in the capsule, reduce the probability of posterior capsule opacification, achieve excellent imaging quality, ensure timely unfolding of the IOL after implantation into the eye, and prevent adhesion of the support haptics and the effective optical area. Therefore, those skilled in the art needs a posterior chamber IOL with an obviously backwardly convex effective optical area, which can improve undesirable imaging quality of the backwardly convex IOL in the prior art.

SUMMARY OF THE INVENTION

The present invention is proposed in view of the above technical problems. The primary goal of the present invention is to provide a posterior chamber IOL with an obviously convex effective optical area posterior surface, which can improve stability of a spatial position of the intraocular lens in a capsule bag and facilitate reduction of an incidence rate of secondary cataract (PCO) after implantation of the intraocular lens; on this basis, a further goal of the present invention is to provide a posterior chamber IOL with an obviously convex effective optical area posterior surface, which can meanwhile improve IOL imaging quality and/or improve visual quality of astigmatism sufferer.

Definitions of Terms

The term "optic" used in the present application consists of an effective optical area and an effective optical area edge of the IOL.

The term "effective optical area" used in the present application refers to the part which is located at the center of the IOL optic, has optical properties and thereby can achieve a major function of adjusting IOL diopter. Specifically speaking, the optic of the IOL used in the embodiments of the present invention has a diameter of about 6 mm, wherein the effective optical area refers to the part within an aperture 5.0 mm of the IOL.

The term "effective optical area edge" used in the present application refers to an edge area which is disposed around the IOL effective optical area and does not affect the optical properties of the IOL. Specifically, the diameter of the optic of the IOL used in embodiments of the present application is about 6 mm, wherein the effective optical area edge refers to an effective optical area edge portion beyond 2.5 mm away from the center of the effective optical area (or IOL aperture 5.0 mm), as designated by the reference number 4 in FIG. 3. Those skilled in the art can easily appreciate that regarding the IOLs having the diameter of the effective optical area in other dimensions, the distance of the effective optical area edge away from the center of the effective optical area might vary correspondingly.

The term "effective optical area posterior surface" used in the present application refers to the effective optical area surface in contact with the human eye posterior capsule after implantation of the IOL into the human eye.

The term "effective optical area anterior surface" used in the present application refers to the effective optical area surface farther away from the posterior capsule opposite to the effective optical area posterior surface after implantation of the IOL into the human eye.

The term "haptics" or "support haptics" used in the present application refers to a portion which is connected to the IOL optic and functions to support the optic and transfer the retraction force generated by the retraction and varicosity of the ciliary muscle to the optic.

The term "haptic root" used in the present application refers to an extension section of one end of the IOL haptic directly connected to the effective optical area edge or (transition connection section if any).

The term "haptic angle" used in the present application refers to an angle of a longitudinal center line of the IOL haptic root relative to a longitudinal center line of the IOL optic in a state that the IOL is not subjected to force, and is represented by the reference sign α, and may also be called "haptic design angle" in the present application, as shown in FIG. 22.

The term "transition connection section inclination angle" used in the present application refers to an angle of a longitudinal center line of the transition connection section relative to the longitudinal center line of the IOL optic, and is represented by the reference sign β, as shown in FIG. 22.

Positional terms "anterior" and "posterior" indicative of orientation relationship used in the present application are relative to the distance away from the human eye posterior capsule. For example, as far as a focusing IOL for adjusting double optical surfaces is concerned, "effective optical area posterior surface" refers to an optical surface closer to the human eye posterior capsule than "effective optical area anterior surface".

The terms "convex" and "concave" indicative of shape used in the present application are relative to a longitudinal central plane of the IOL optic. For example, "rearwardly convex IOL" means that a point on the IOL effective optical area posterior surface closer to the center of the surface is farther away from the longitudinal central plane of the IOL optic.

The term "effective optical area obviously rearwardly convex" or "effective optical area posterior surface obviously convex" used in the present application are relative. Specifically, the IOL effective optical area posterior surface is more obviously convex than the IOL effective optical area anterior surface. In other words, a radius of curvature of the IOL effective optical area posterior surface is smaller than that of the IOL effective optical area anterior surface. Those skilled in the art appreciate that the terms "effective optical area obviously rearwardly convex" or "effective optical area posterior surface obviously convex" for example may also be called "effective optical area highly rearward convex".

The term "basic spherical surface" used in the present application refers to a spherical surface corresponding to various the surface shapes utilized by the IOL effective optical area anterior and posterior surface of the IOL in the present invention. In the present application, to make the terms consistent, the spherical surface is collectively called "basic spherical surface".

Since the obviously rearwardly convex posterior chamber IOL effective optical area anterior surface or posterior surface having a high order aspherical surface design in the present application is forwardly or rearwardly convex, the term "effective optical area surface apex" used in the present application refers to a center point of the IOL convex effective optical area anterior surface or the IOL convex effective optical area posterior surface. That is to say, the 'effective optical area surface apex" refers to a center point of the IOL convex effective optical area anterior surface farthest away from the longitudinal central plane of the IOL optic; or a point of the IOL convex effective optical area posterior surface farthest away from the longitudinal central plane of the IOL optic.

The effective optical area anterior surface of the obviously rearwardly convex Toric posterior chamber IOL in the present application has a convex toric surface design, and the IOL effective optical area anterior surface is forwardly convex. Therefore, as far as the Toric posterior chamber IOL in the present application, the term "effective optical area anterior surface apex" used in the present application refers to a point of the IOL convex effective optical area posterior surface farthest away from the longitudinal central plane of the IOL optic.

According to an aspect of the present invention, there is provided a posterior chamber intraocular lens, comprising: an optic consisting of an effective optical area and an effective optical area edge; at least two haptics connected to the optic, characterized in that a posterior surface of the effective optical area is a convex spherical surface and has a radius of curvature in a range of 6.6 mm-80.0 mm.

In a preferred embodiment of the present invention, an anterior surface of the effective optical area is a convex spherical surface and has a radius of curvature in a range of 7.1 mm-84.0 mm.

In another preferred embodiment of the present invention, the posterior chamber IOL may be made of hydrophobic acrylate, the posterior surface of the effective optical area has a radius of curvature in a range of 7.5 mm-55.0 mm, and the anterior surface of the effective optical area has a radius of curvature in a range of 8.0 mm-74.0 mm. Preferably, the posterior surface of the effective optical area has a radius of curvature in a range of 8.1 mm-19.5 mm. More preferably, the posterior surface of the effective optical area has a radius of curvature about 11.1 mm.

In another preferred embodiment of the present invention, the posterior chamber IOL may be made of hydrophobic acrylate, the posterior surface of the effective optical area has a radius of curvature in a range of 7.0 mm-70.0 mm, and the anterior surface of the effective optical area has a radius of curvature in a range of 17.0 mm-73.0 mm. Preferably, the posterior surface of the effective optical area has a radius of curvature in a range of 7.6 mm-16.5 mm. More preferably, the posterior surface of the effective optical area has a radius of curvature about 10.6 mm.

In a further preferred embodiment of the present invention, the posterior chamber IOL may be made of silicone or hydrogel, the posterior surface of the effective optical area has a radius of curvature in a range of 6.6 mm-48.0 mm, and the anterior surface of the effective optical area has a radius of curvature in a range of 7.1 mm-48.6 mm. Preferably, the posterior surface of the effective optical area has a radius of curvature in a range of 7.5 mm-10.0 mm. More preferably, the posterior surface of the effective optical area has a radius of curvature about 8.0 mm.

In another preferred embodiment of the present invention, the posterior chamber IOL may be made of hydrophobic acrylate, the posterior surface of the effective optical area has a radius of curvature in a range of 7.0 mm-52.0 mm, and the anterior surface of the effective optical area has a radius of curvature in a range of 7.8 mm-59.0 mm. Preferably, the posterior surface of the effective optical area has a radius of curvature in a range of 7.0 mm-11.0 mm. More preferably, the posterior surface of the effective optical area has a radius of curvature about 8.5 mm.

In another preferred embodiment of the present invention, the posterior chamber IOL may be made of polymethyl methacrylate (PMMA), the posterior surface of the effective optical area has a radius of curvature in a range of 6.8 mm-59.5 mm, and the anterior surface of the effective optical area has a radius of curvature in a range of 10.9 mm-60.0 mm. Preferably, the posterior surface of the effective optical area has a radius of curvature in a range of 7.0 mm-13.1 mm. More preferably, the posterior surface of the effective optical area has a radius of curvature about 9.0 mm.

In another preferred embodiment of the present invention, the posterior chamber IOL may be made of hydrophobic acrylate, the posterior surface of the effective optical area has a radius of curvature in a range of 7.0 mm-66.0 mm, and the anterior surface of the effective optical area has a radius of curvature in a range of 14.4 mm-74.0 mm. Preferably, the posterior surface of the effective optical area has a radius of curvature in a range of 7.2 mm-15.3 mm. More preferably, the posterior surface of the effective optical area has a radius of curvature about 9.9 mm.

In another preferred embodiment of the present invention, the posterior chamber IOL may be made of hydrophobic acrylate, the posterior surface of the effective optical area has a radius of curvature in a range of 7.0 mm-80.0 mm, and the anterior surface of the effective optical area has a radius of curvature in a range of 30.8 mm-84.0 mm. Preferably, the posterior surface of the effective optical area has a radius of curvature in a range of 9.0 mm-20.3 mm. More preferably, the posterior surface of the effective optical area has a radius of curvature about 12.7 mm.

In another preferred embodiment of the present invention, the radius of curvature of the posterior surface of the effective optical area may be smaller than that of the anterior surface of the effective optical area.

Preferably, the radius of curvature of the posterior surface of the effective optical area may be 17.8%-60.0% of the radius of curvature of the anterior surface of the effective optical area.

More preferably, the radius of curvature of the posterior surface of the effective optical area may be 20.0%-45.6% of the radius of curvature of the anterior surface of the effective optical area.

In another preferred embodiment of the present invention, the posterior chamber IOL may be a one-piece IOL.

In another preferred embodiment of the present invention, the posterior chamber IOL may be a three-piece IOL.

In another preferred embodiment of the present invention, the haptics are symmetrically connected to the effective optical area edge around a circumferential direction of the optic.

According to another aspect of the present invention, there is provided a posterior chamber t intraocular lens IOL, comprising:

an optic consisting of an effective optical area and an effective optical area edge;
at least two haptics connected to the optic,
characterized in that an anterior surface of the effective optical area is a convex spherical surface and a posterior surface of the effective optical area is a convex aspherical surface adopting a higher order aspherical surface, the convex aspherical surface is formed by a basic spherical surface with a radius of curvature in a range of 6.6 mm-80.0 mm superimposed with an offset amount relative to the basic spherical surface, a two-dimensional coordinate system is established with an effective optical area surface apex adopting a higher order aspherical surface design in the posterior chamber IOL as an original point, a longitudinal coordinate axis Y of the coordinate system is tangential with the effective optical area surface and passes through the effective optical area surface apex O; a horizontal coordinate axis Z of the coordinate system is parallel to an ocular axis direction D-D' and is at an angle of 90 degrees relative to the longitudinal coordinate axis Y and passes through the effective optical area surface apex O, a curve of the convex aspherical surface on the two-dimensional coordinate system plane YZ satisfies the following expression of higher order aspherical surface design:

$$Z(y) = \frac{cy^2}{1+\sqrt{1-c^2y^2}} + \sum_{i=m}^{n} A_{2i} \cdot y^{2i}$$

Wherein $Z(y)$ is an expression of the curve of the aspherical surface of the IOL effective optical area on the YZ plane, c is a reciprocal of a radius of curvature of the surface of the basic spherical surface of the effective optical area, y is a vertical distance of any point on the curve from the horizontal coordinate axis Z, $A_{2i}$ is a higher-order term coefficient of the aspherical surface, m, n are both an integer greater than or equal to 1 and n≥m, Points on the convex aspherical surface are obtained in a way that the curve rotates around the horizontal coordinate axis (Z) for symmetry variation.

In an preferred embodiment of the present invention, the radius of curvature of the anterior surface of the effective optical area is in a range of 7.1 mm-84.0 mm.

In another preferred embodiment of the present invention, m is 2 and n is 5.

In another preferred embodiment of the present invention, $A_4$=2.431E-004, $A_6$=2.897E-004, $A_8$=-5.417E-005, $A_{10}$=2.940E-006.

In another preferred embodiment of the present invention, the posterior chamber IOL is made of hydrophobic acrylate with a refractive index 1.48, the basic spherical surface of the posterior surface of the effective optical area has a radius of curvature in a range of 7.5 mm-55.0 mm, and the anterior surface of the effective optical area has a radius of curvature in a range of 8.0 mm-74.0 mm.

In a further preferred embodiment of the present invention, the basic spherical surface of the posterior surface of the effective optical area has a radius of curvature in a range of 8.1 mm-19.5 mm.

In a further preferred embodiment of the present invention, the basic spherical surface of the posterior surface of the effective optical area has a radius of curvature 11.1 mm.

In a further preferred embodiment of the present invention, a radius of curvature of the basic spherical surface of the posterior surface of the effective optical area is smaller than that of the anterior surface of the effective optical area.

In a further preferred embodiment of the present invention, a radius of curvature of the basic spherical surface of the posterior surface of the effective optical area is 17.8%-60.0% of the radius of curvature of the anterior surface of the effective optical area.

In a further preferred embodiment of the present invention, a radius of curvature of the basic spherical surface of the posterior surface of the effective optical area is 20.0%-45.6% of the radius of curvature of the anterior surface of the effective optical area.

According to another aspect of the present invention, there is provided a posterior chamber intraocular lens IOL, comprising:

an optic consisting of an effective optical area and an effective optical area edge;

at least two haptics connected to the optic, characterized in that an anterior surface of the effective optical area is a convex spherical surface and an anterior surface of the effective optical area is a convex aspherical surface adopting a higher order aspherical surface design, the convex aspherical surface is formed by a basic spherical surface with a radius of curvature in a range of 7.1 mm-84.0 mm superimposed with an offset amount relative to the basic spherical surface, and a radius of curvature of the posterior surface of the effective optical area is in a range of 6.6 mm-80.0 mm.

A two-dimensional coordinate system is established with an effective optical area surface apex adopting a higher order aspherical surface design in the posterior chamber IOL as an original point, a longitudinal coordinate axis Y of the coordinate system is tangential with the effective optical area surface and passes through the effective optical area surface apex O; a horizontal coordinate axis Z of the coordinate system is parallel to an ocular axis direction D-D' and is at an angle of 90 degrees relative to the longitudinal coordinate axis Y and passes through the effective optical area surface apex O, a curve of the convex aspherical surface on the two-dimensional coordinate system plane YZ satisfies the following expression of higher order aspherical surface design:

$$Z(y) = \frac{cy^2}{1+\sqrt{1-c^2y^2}} + \sum_{i=m}^{n} A_{2i} \cdot y^{2i}$$

Wherein Z(y) is an expression of the curve of the aspherical surface of the IOL effective optical area on the YZ plane, c is a reciprocal of a radius of curvature of the surface of the basic spherical surface of the effective optical area, y is a vertical distance of any point on the curve from the horizontal coordinate axis Z, $A_{2i}$ is a higher-order term coefficient of the aspherical surface, m, n are both an integer greater than or equal to 1 and n≥m, Points on the convex aspherical surface are obtained in a way that the curve rotates around the horizontal coordinate axis (Z) for symmetry variation.

In another preferred embodiment of the present invention, m is 2 and n is 5.

In another preferred embodiment of the present invention, $A_4$=−2.431E−004, $A_6$=−2.897E−004, $A_8$=5,417E−005, $A_{10}$=−2.940E−006.

In another preferred embodiment of the present invention, the posterior chamber IOL is made of hydrophobic acrylate with a refractive index 1.48, the posterior surface of the effective optical area has a radius of curvature in a range of 7.5 mm-55.0 mm, and the basic spherical surface of the anterior surface of the effective optical area has a radius of curvature in a range of 8.0 mm-74.0 mm.

In a further preferred embodiment of the present invention, the posterior surface of the effective optical area has a radius of curvature in a range of 8.1 mm-19.5 mm.

In a further preferred embodiment of the present invention, the posterior surface of the effective optical area has a radius of curvature 11.1 mm.

In a further preferred embodiment of the present invention, a radius of curvature of the posterior surface of the effective optical area is smaller than that of the basic spherical surface of the anterior surface of the effective optical area.

In a further preferred embodiment of the present invention, a radius of curvature of the posterior surface of the effective optical area is 17.8%-60.0% of the radius of curvature of the basic spherical surface of the anterior surface of the effective optical area.

In a further preferred embodiment of the present invention, a radius of curvature of the posterior surface of the effective optical area is 20.0%-45.6% of the radius of curvature of the basic spherical surface of the anterior surface of the effective optical area.

According to a further aspect of the present invention, there is provided a posterior chamber intraocular lens IOL, comprising:

an optic consisting of an effective optical area and an effective optical area edge;

at least two haptics connected to the optic, characterized in that an anterior surface of the effective optical area is a convex toric surface, the convex toric surface is formed by a basic spherical surface with a radius of curvature in a range of 7.1 mm-84.0 mm superimposed with an offset amount relative to the basic spherical surface, and a radius of curvature of the posterior surface of the effective optical area is in a range of 6.6 mm-80.0 mm.

A two-dimensional coordinate system is established with an effective optical area anterior surface apex in the posterior chamber IOL as an original point, a longitudinal coordinate axis Y of the coordinate system is tangential with the effective optical area anterior surface and passes through the effective optical area anterior surface apex O; a horizontal coordinate axis Z of the coordinate system is parallel to an ocular axis direction D-D' and is at an angle of 90 degrees relative to the longitudinal coordinate axis Y and passes through the effective optical area anterior surface apex O, and a curve of the convex toric surface on the two-dimensional coordinate system plane YZ satisfies the following expression:

$$Z(y) = \frac{cy^2}{1+\sqrt{1-(1+k)c^2y^2}} + \sum_{i=m}^{n} A_{2i} \cdot y^{2i}$$

Wherein Z(y) is an expression of the curve of the toric surface of the IOL effective optical area on the YZ plane, c is a reciprocal of a radius of curvature of the surface of the basic spherical surface of the effective optical area, y is a vertical distance of any point on the curve from the horizontal coordinate axis Z, $A_{2i}$ is a higher-order term coefficient of the aspherical surface, m, n are both an integer greater than or equal to 1 and n≥m, Points on the convex toric surface are obtained in a way that the curve rotates about a straight line parallel to the longitudinal coordinate axis Y one round with a certain anterior surface rotation radius R.

In another preferred embodiment of the present invention, the posterior chamber IOL is made of hydrophobic acrylate with a refractive index 1.48, the posterior surface of the effective optical area has a radius of curvature in a range of 7.5 mm-55.0 mm, and the basic spherical surface of the anterior surface of the effective optical area has a radius of curvature in a range of 8.0 mm-74.0 mm.

In a further preferred embodiment of the present invention, the posterior surface of the effective optical area has a radius of curvature in a range of 8.1 mm-19.5 mm.

In a further preferred embodiment of the present invention, the posterior surface of the effective optical area has a radius of curvature 11.1 mm.

In a further preferred embodiment of the present invention, a radius of curvature of the posterior surface of the effective optical area is smaller than that of the basic spherical surface of the anterior surface of the effective optical area.

In a further preferred embodiment of the present invention, a radius of curvature of the posterior surface of the effective optical area is 17.8%-60.0% of the radius of curvature of the basic spherical surface of the anterior surface of the effective optical area.

In a further preferred embodiment of the present invention, a radius of curvature of the posterior surface of the effective optical area is 20.0%-45.6% of the radius of curvature of the basic spherical surface of the anterior surface of the effective optical area.

In a further preferred embodiment of the present invention, the radius of curvature of a basic curve of the effective optical area anterior surface on the YZ plane is in a range of 8.0 mm-74.0 mm; when an additional astigmatic power of the toric surface is in a range of 1.0D-4.0D, a magnitude of the anterior surface rotation radius is in a range of 8.2 mm-39.95 mm.

In another preferred embodiment of the present invention, the posterior chamber IOL may be a one-piece IOL.

In another preferred embodiment of the present invention, the posterior chamber IOL may be a three-piece IOL.

In another preferred embodiment of the present invention, the haptics are symmetrically connected to the effective optical area edge around a circumferential direction of the optic.

According to a further aspect of the present invention, there is provided a posterior chamber intraocular lens IOL, comprising:

an optic consisting of an effective optical area and an effective optical area edge;

at least two haptics connected to the optic, characterized in that an anterior surface of the effective optical area is a toric surface;

a posterior surface of the effective optical area is an aspherical surface.

In a further preferred embodiment of the present invention, the toric surface is a convex toric surface, and the convex toric surface is formed by a basic spherical surface with a radius of curvature in a range of 5.5 mm-84.0 mm superimposed with an offset amount relative to the basic spherical surface.

A two-dimensional coordinate system is established with an effective optical area anterior surface apex (O) in the posterior chamber IOL as an original point, a longitudinal coordinate axis Y of the coordinate system is tangential with the effective optical area anterior surface and passes through the effective optical area anterior surface apex (O); a horizontal coordinate axis (Z) of the coordinate system is parallel to an ocular axis direction D-D' and is at an angle of 90 degrees relative to the longitudinal coordinate axis (Y) and passes through the effective optical area anterior surface apex (O), and a curve of the convex toric surface on the two-dimensional coordinate system plane (YZ) satisfies the following expression:

$$Z(y) = \frac{cy^2}{1 + \sqrt{1 - (1+k)c^2 y^2}} + \sum_{i=m}^{n} A_{2i} \cdot y^{2i}$$

Wherein $Z(y)$ is an expression of the curve of the convex toric surface of the IOL effective optical area on the YZ plane, c is a reciprocal of a radius of curvature of the surface of the basic spherical surface of the effective optical area anterior surface, y is a vertical distance of any point on the curve from the horizontal coordinate axis (Z), $A_{2i}$ is a higher-order term coefficient of the aspherical surface, m, n are both an integer greater than or equal to 1 and n≥m, Points on the convex toric surface are obtained in a way that the curve rotates about a straight line (d-d') parallel to the longitudinal coordinate axis (Y) one round with a certain anterior surface rotation radius (R).

In a further preferred embodiment of the present invention, the asphericla surface is a convex aspherical surface, and the basic spherical surface of the convex aspherical surface has a radius of curvature in a range of 8.0 mm-74.0 mm.

In a further preferred embodiment of the present invention, the convex aspherical surface adopts a higher order aspherical surface design.

A two-dimensional coordinate system is established with an effective optical area anterior surface apex adopting the higher order aspherical surface design in the posterior chamber IOL as an original point, a longitudinal coordinate axis (Y) of the coordinate system is tangential with the effective optical area posterior surface and passes through the effective optical area posterior surface apex (O'); a horizontal coordinate axis (Z) of the coordinate system is parallel to an ocular axis direction (D-D') and is at an angle of 90 degrees relative to the longitudinal coordinate axis (Y) and passes through the effective optical area posterior surface apex (O'), and a curve of the convex aspherical surface on the two-dimensional coordinate system plane (YZ) satisfies the following higher order aspherical surface expression:

$$Z(y) = \frac{cy^2}{1 + \sqrt{1 - c^2 y^2}} + \sum_{i=m}^{n} A_{2i} \cdot y^{2i}$$

Wherein $Z(y)$ is an expression of the curve of the aspherical surface of the IOL effective optical area on the YZ plane, c is a reciprocal of a radius of curvature of the surface of the basic spherical surface of the effective optical area, y is a vertical distance of any point on the curve from the horizontal coordinate axis (Z), $A_{2i}$ is a higher-order term coefficient of the aspherical surface, m, n are both an integer greater than or equal to 1 and n≥m, Points on the convex aspherical surface are obtained in a way that the curve rotates around the horizontal coordinate axis (Z) for symmetry variation.

In a further preferred embodiment of the present invention, a radius of curvature of the basic spherical surface of the convex aspherical surface is smaller than that of the basic spherical surface of the convex toric surface.

In a further preferred embodiment of the present invention, the posterior chamber IOL is made of hydrophobic acrylate with a refractive index 1.48.

In a further preferred embodiment of the present invention, the haptics are L-shaped haptics or C-shaped haptics, and the haptic angle is 1.5°.

In a further preferred embodiment of the present invention, the haptics are two haptics symmetrically arranged around a circumferential direction of the optic.

Specifically, the present invention relates to content in the following aspect:

1. A posterior chamber intraocular lens comprising:
an optic consisting of an effective optical area and an effective optical area edge;
at least two haptics connected to the optic,
characterized in that
a posterior surface of the effective optical area is a convex surface, and a basic spherical surface thereof has a radius of curvature in a range of 6.6 mm-80.0 mm.

2. The posterior chamber IOL according to technical solution 1, characterized in that an anterior surface of the effective optical area is a convex surface, and a basic spherical surface thereof has a radius of curvature in a range of 7.1 mm-84.0 mm.

3. The posterior chamber IOL according to technical solution 1 or 2, characterized in that a radius of curvature of the basic spherical surface of the posterior surface of the effective optical area is smaller than that of the anterior surface of the effective optical area.

4. The posterior chamber IOL according to technical solution 3, characterized in that the radius of curvature of the basic spherical of the posterior surface of the effective optical area is 17.8%-60.0% of the radius of curvature of the anterior surface of the effective optical area.

5. The posterior chamber IOL according to technical solution 4, characterized in that, the radius of curvature of the basic spherical surface of the posterior surface of the effective optical area is 20.0%-45.6% of the radius of curvature of the anterior surface of the effective optical area.

6. The posterior chamber IOL according to technical solution 3, characterized in that the roots of the haptics are directly connected to the effective optical area edge of the optic.

7. The posterior chamber IOL according to technical solution 6, characterized in that, the effective optical area edge further comprises a sharp bend.

8. The posterior chamber IOL according to technical solution 3, characterized in that, the posterior chamber IOL further comprises a transition connection section, and the roots of the haptics are connected to the effective optical area edge of the optic via the transition connection section.

9. The posterior chamber IOL according to technical solution 8, characterized in that, the effective optical area edge further comprises a sharp bend.

10. The posterior chamber IOL according to technical solution 8 or 9, characterized in that, a longitudinal center line of the transition connection section is at a transition connection section inclination angle in a range of 10°-45° relative to a longitudinal center line of the optic.

11. The posterior chamber IOL according to any one of technical solutions 6-10, characterized in that, a longitudinal center line of the haptic roots is at a haptic angle in a range of 0°-7° relative to the longitudinal center line of the optic.

12. The posterior chamber IOL according to any one of technical solutions 1-11, characterized in that, the surface shape of the posterior surface of the effective optical area comprises one of spherical surface, aspherical surface, toric surface, multi-focal surface of multi-area refraction design and multi-focal surface of multi-area diffraction design.

13. The posterior chamber IOL according to any one of technical solutions 1-11, characterized in that, the surface shape of the anterior surface of the effective optical area comprises one of spherical surface, aspherical surface, toric surface, multi-focal surface of multi-area refraction design and multi-focal surface of multi-area diffraction design.

14. The posterior chamber IOL according to any one of the preceding technical solutions, characterized in that, the posterior chamber IOL is made of silicone, hydrogel, hydrophobic acrylate or polymethyl methacrylate.

15. The posterior chamber IOL according to technical solution 14, characterized in that, a material for preparing the posterior chamber IOL has a refractive index in a range between 1.45 and 1.56.

16. The posterior chamber IOL according to technical solution 14 or 15, characterized in that, the posterior chamber IOL is made of hydrophobic acrylate with a refractive index of 1.48, the basic spherical surface of the posterior surface of the effective optical area has a radius of curvature in a range of 7.5 mm-55.0 mm, and the anterior surface of the effective optical area has a radius of curvature in a range of 8.0 mm-74.0 mm.

17. The posterior chamber IOL according to technical solution 16, characterized in that, the basic spherical surface of the posterior surface of the effective optical area has a radius of curvature in a range of 8.1 mm-19.5 mm.

18. The posterior chamber IOL according to technical solution 17, characterized in that, the basic spherical surface of the posterior surface of the effective optical area has a radius of curvature of 11.1 mm.

19. The posterior chamber IOL according to any one of technical solutions 1-18, characterized in that, the posterior chamber IOL is a one-piece IOL.

20. The posterior chamber IOL according to any one of technical solutions 1-18, characterized in that, the posterior chamber IOL is a three-piece IOL.

As compared with the posterior chamber IOL in the prior art, the effective optical area of the posterior chamber IOL of the invention adopts a design with the posterior surface obviously convex and optionally additionally adopts a design such as aspherical surface, higher order aspherical surface, toric surface, multi-focal surface of multi-area refraction design and multi-focal surface of multi-area diffraction design, which reduces the distance between the posterior surface of the effective optical area of the IOL and the posterior capsule, improves the stability of a spatial position of the IOL in a capsule bag, fully embodies the advantages of the right-angle edge effect of the IOL optical effective area edge, and reduces an incidence rate of posterior capsule opacification (PCO) after implantation of the IOL; since the effective optical area anterior surface is relatively flat, the IOL haptics (particularly with haptics of the one-piece posterior chamber IOL) will not be tightly pressed on the effective optical area anterior surface upon folding, the haptics are more easily unfolded after implantation into the eye and the support haptics are not mutually adhered to the effective optical area, and meanwhile the IOL imaging quality can be improved and/or the visual quality of the astigmatism sufferer is enhanced.

BRIEF DESCRIPTION OF PREFERRED EMBODIMENTS

The features and advantages will be made more apparent according to the following figures and description, wherein:

FIG. 1 schematically illustrates a basic composition of a human eye refractive system;

FIG. 2 schematically illustrates a graph showing the distribution of spherical aberration magnitude ($\delta L_0'$) of intraocular lenses in the prior art having different surfaces;

FIG. 3 schematically illustrates a perspective view of a one-piece posterior chamber intraocular lens according to an embodiment of the present invention as viewed from above an anterior surface of the intraocular lens, wherein haptics are unfolded and not yet folded onto the anterior surface of the optics of the intraocular lens;

FIG. 4 schematically illustrates a perspective view of a one-piece posterior chamber intraocular lens according to an embodiment of the present invention as viewed above a posterior surface of the intraocular lens, wherein haptics are unfolded and not yet folded onto the anterior surface of the optics of the intraocular lens;

Figure 6:
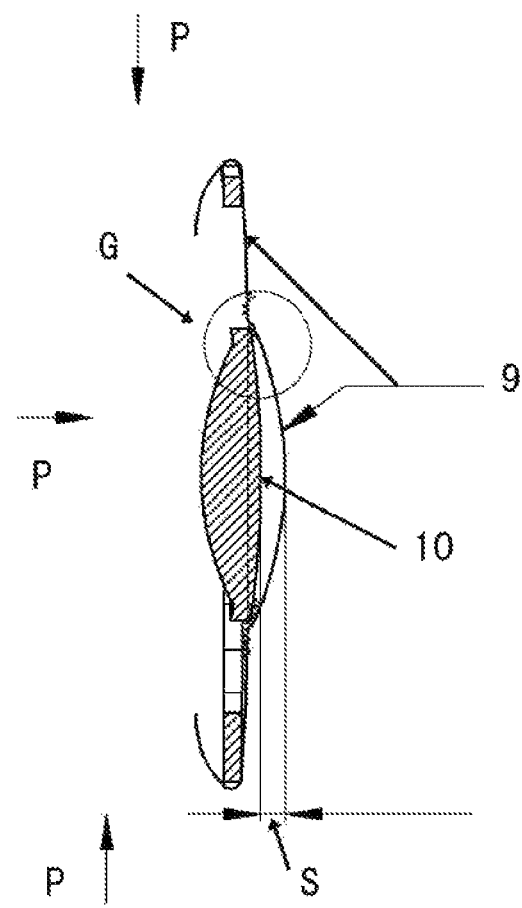
FIG. 6 illustrates a schematic view of interaction relationship between an effective optical area posterior surface and a posterior capsule of a posterior chamber intraocular lens in the prior art implanted into a human eye when a capsulate bag is in a retracted state.
Figure 7:
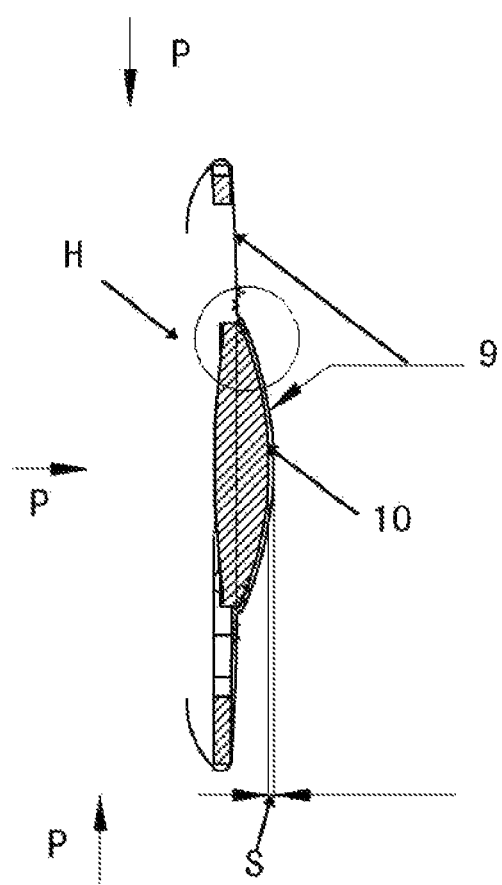
FIG. 7 illustrates a schematic view of interaction relationship between an effective optical area posterior surface and a posterior capsule of a one-piece posterior chamber intraocular lens according to the present invention implanted into a human eye when a capsulate bag is in a retracted state.
Figure 8:
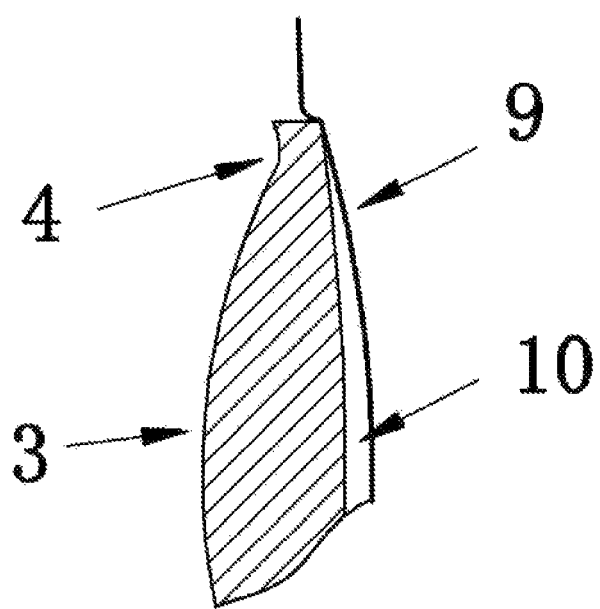
Figure 9:
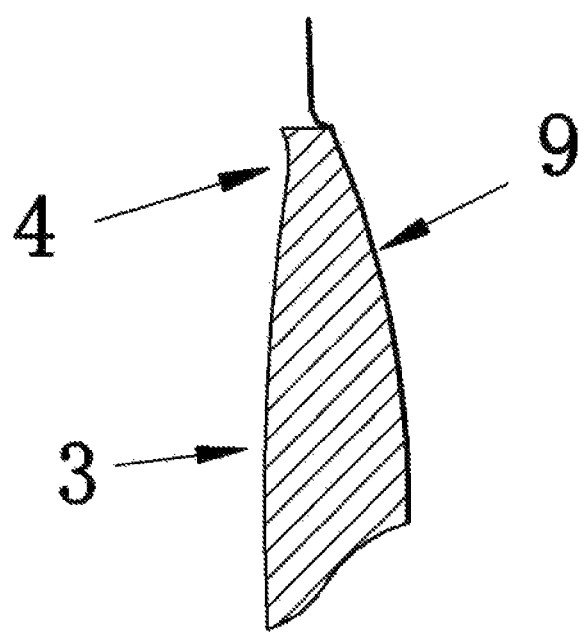
Figure 10:
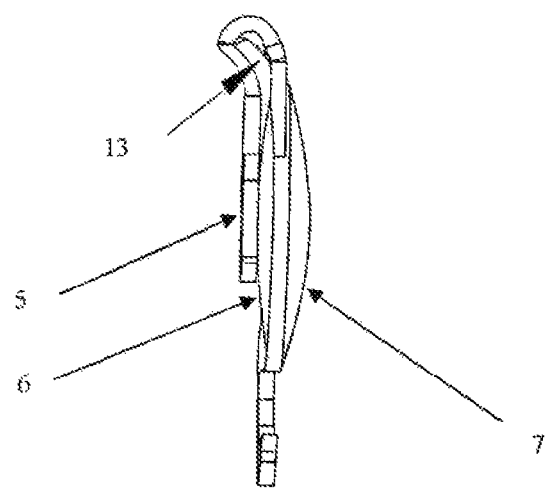
Figure 11:
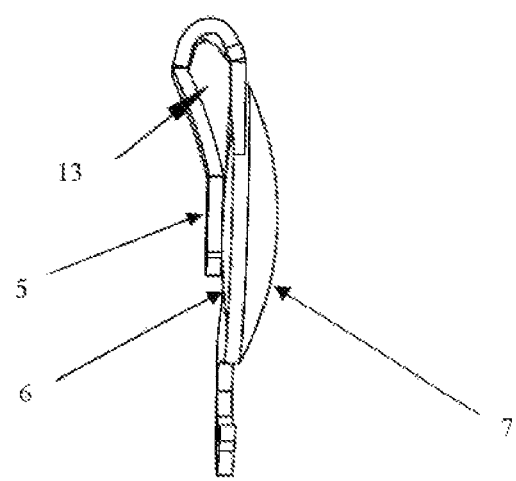
Figure 12:
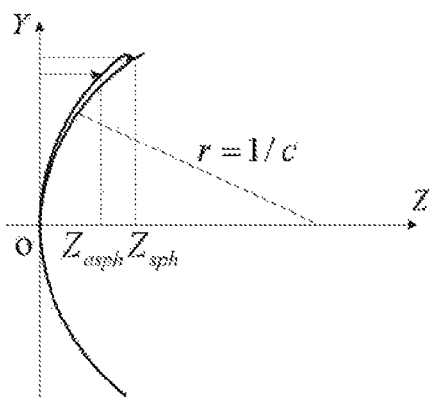
Figure 13:
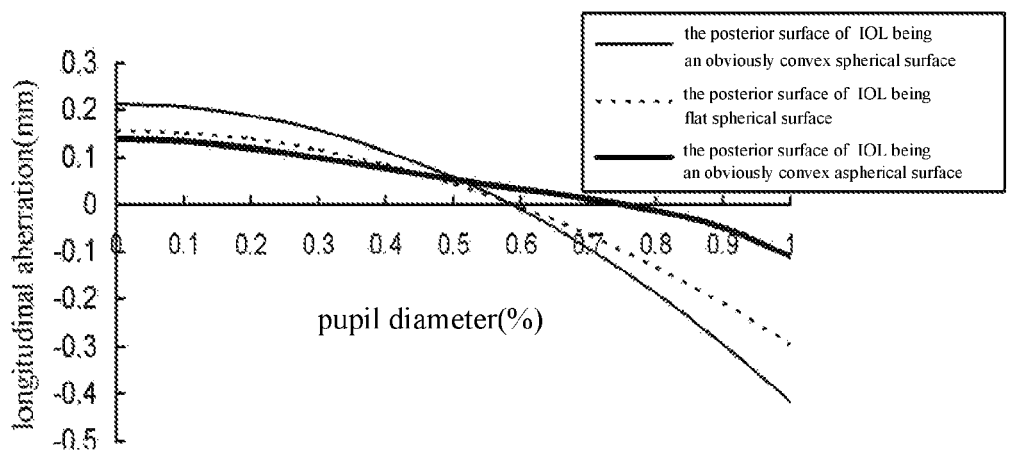
Figure 14A:
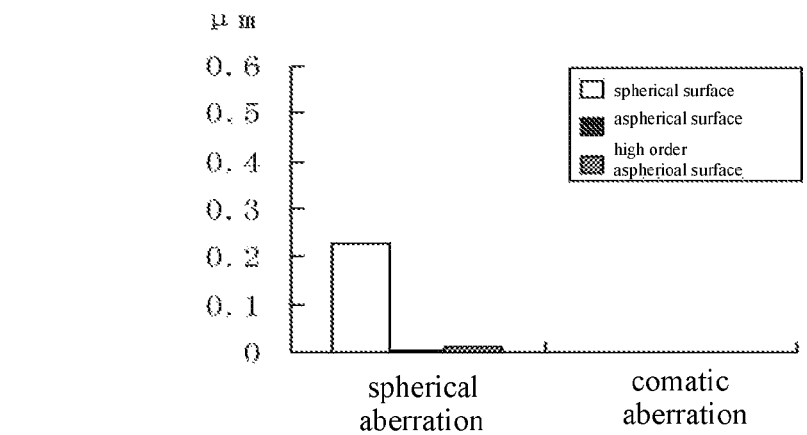
Figure 14B:
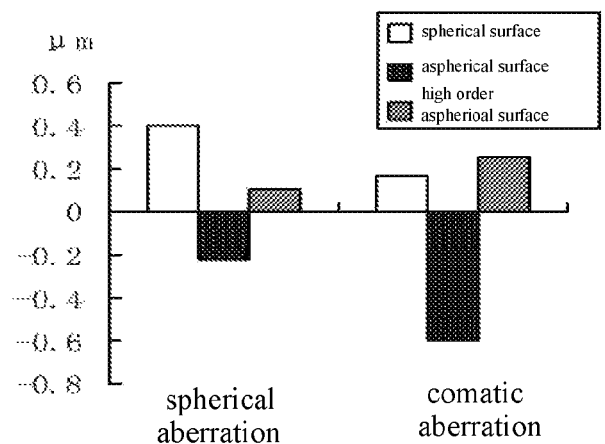
Figure 14C:
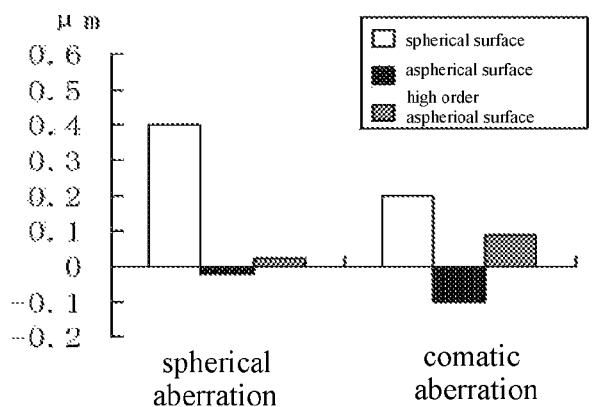
Figure 15:
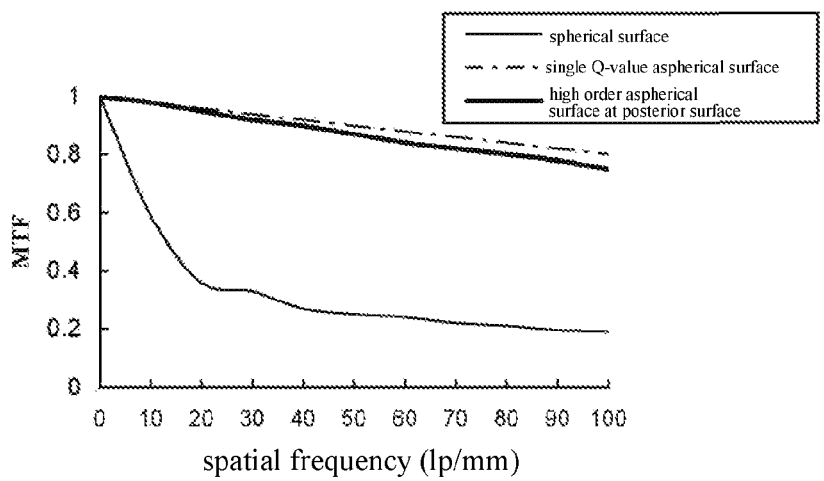
Figure 16:
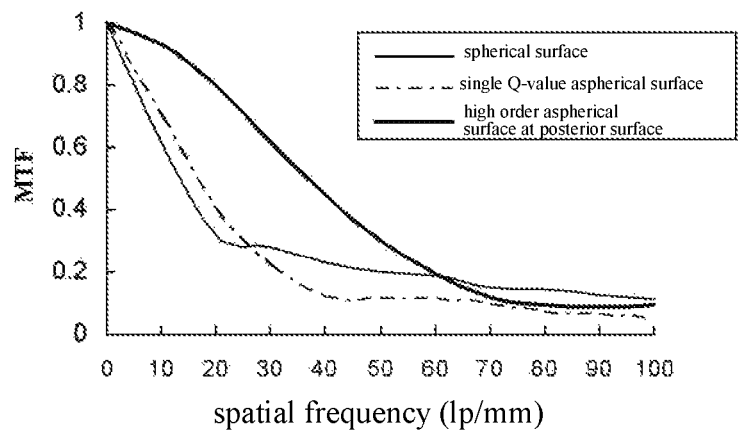
Figure 17:
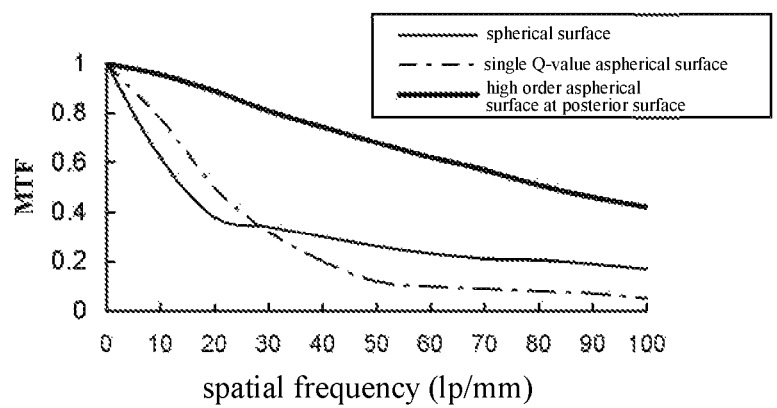
Figure 18:
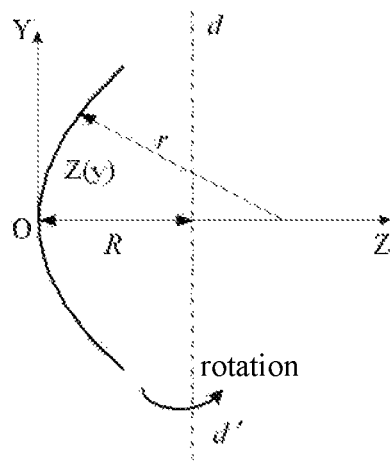
Figure 19A:
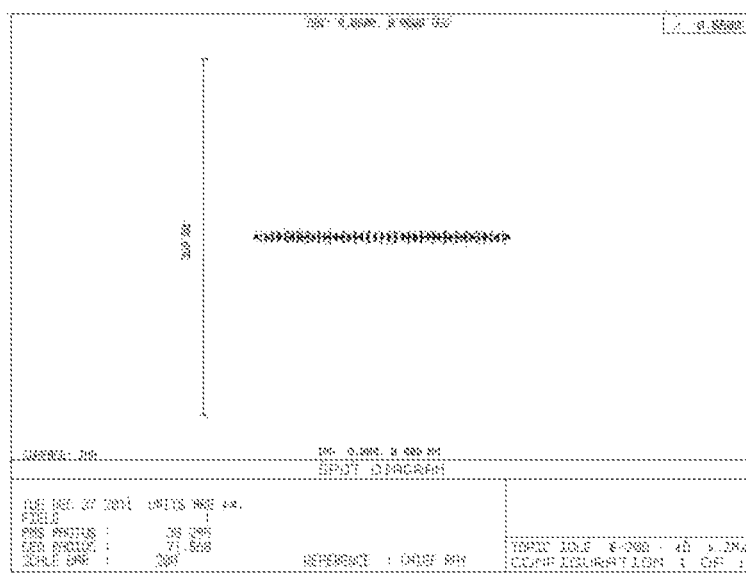
Figure 19B:
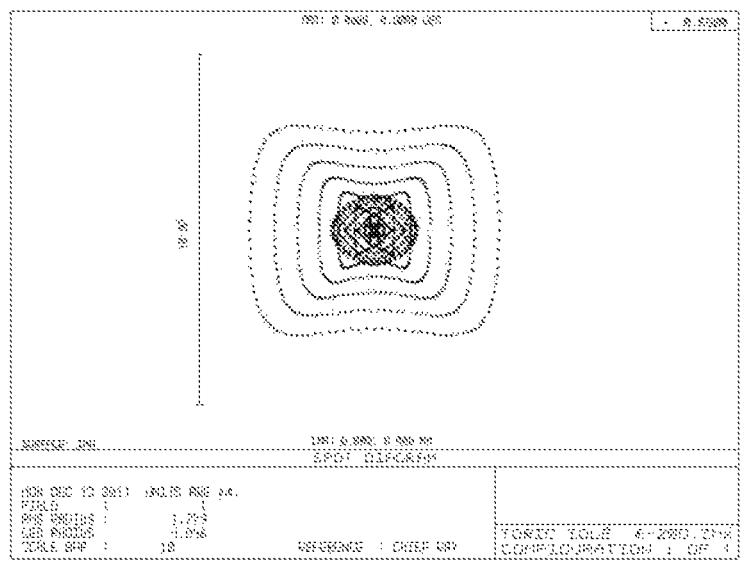
Figure 20A:
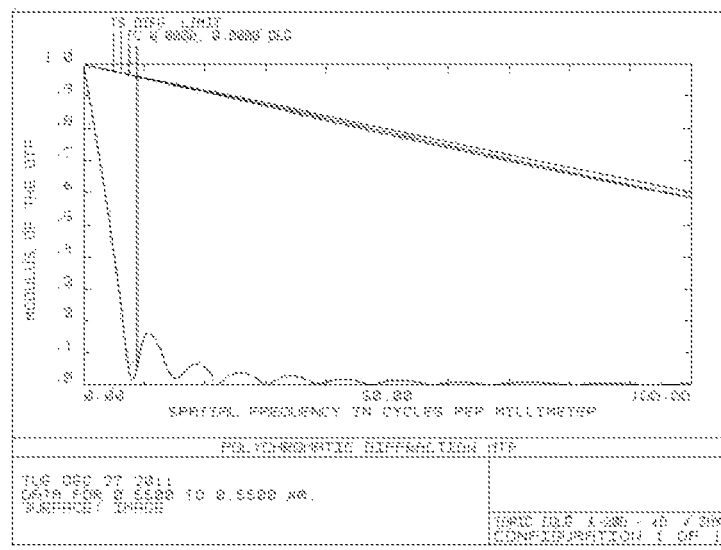
Figure 20B:
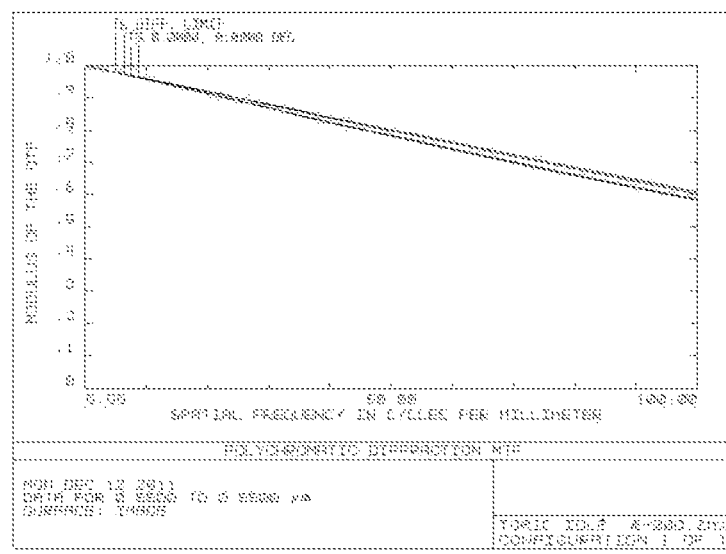
Figure 21:
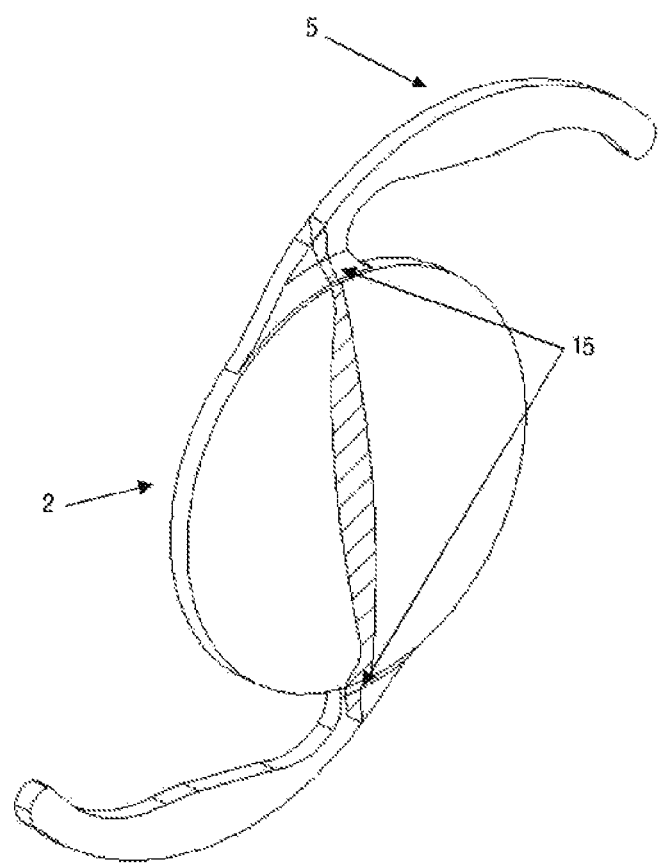
Figure 22:
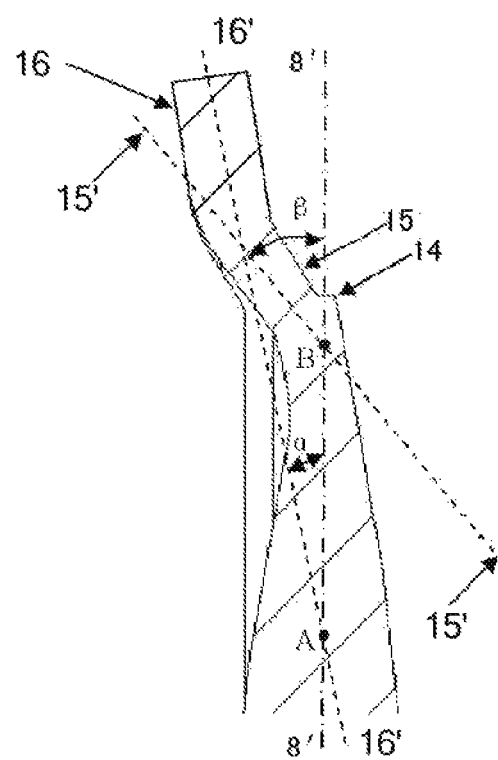
Figure 23:
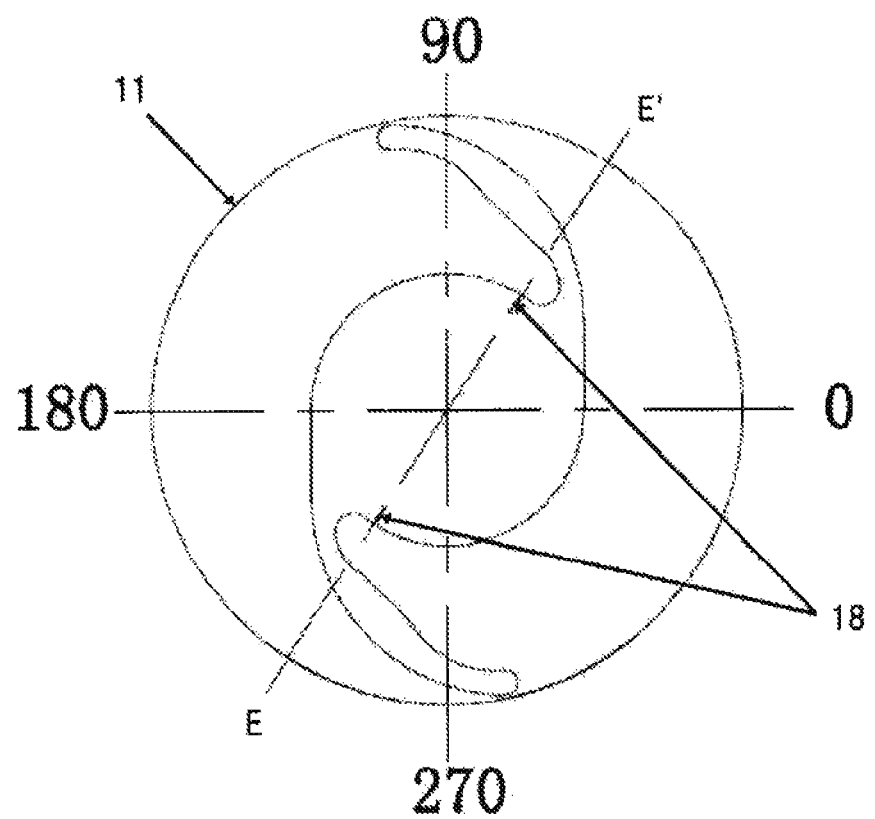
Figure 24:
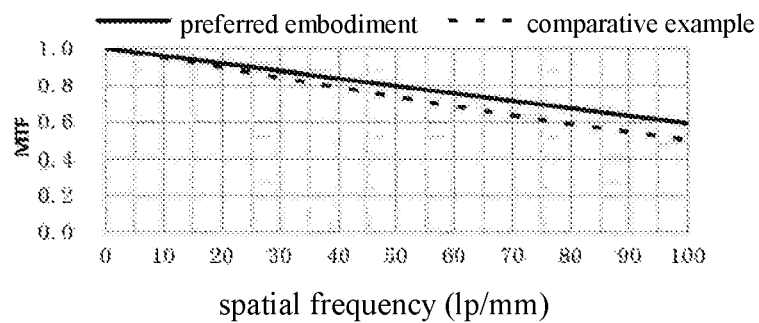
Figure 25:
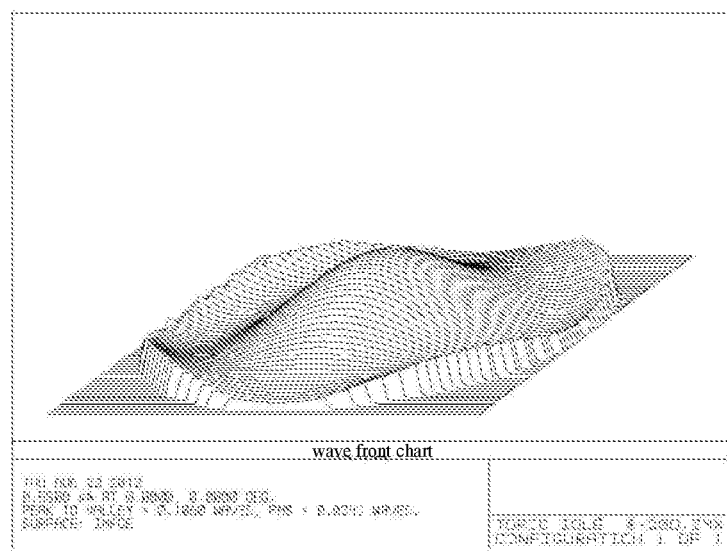
Figure 26:
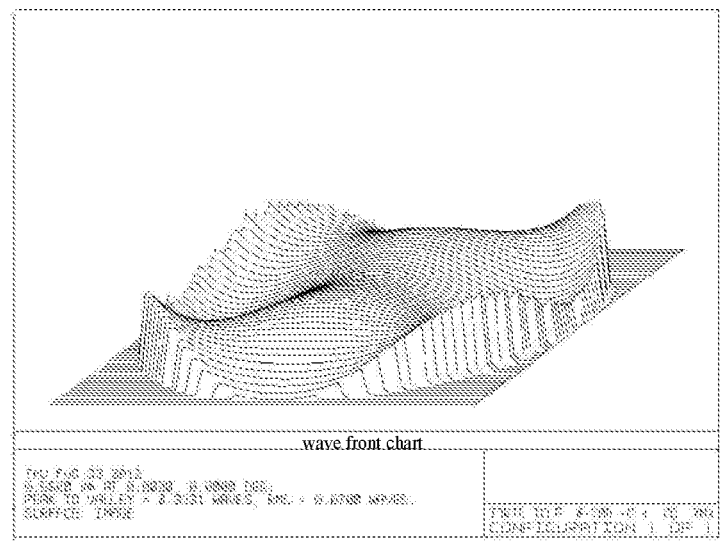

FIG. 8 schematically illustrates interaction relationship between an effective optical area posterior surface and a posterior capsule of a posterior chamber intraocular lens in the prior art as shown in circle G of FIG. 6;

FIG. 9 schematically illustrates interaction relationship between an effective optical area posterior surface and a posterior capsule of a one-piece posterior chamber intraocular lens in the present invention as shown in circle H of FIG. 7;

FIG. 10 schematically illustrates, in the form of a cross sectional view, a situation in which haptics of one-piece posterior chamber intraocular lens in the prior art are folded onto the effective optical area anterior surface before the intraocular lens is implanted into a human eye;

FIG. 11 schematically illustrates, in the form of a cross sectional view, a situation in which haptics of one-piece posterior chamber intraocular lens in the present invention are folded onto the effective optical area anterior surface before the intraocular lens is implanted into a human eye;

FIG. 12 schematically illustrates the difference between an effective optical area surface of a higher order aspherical intraocular lens according to an embodiment of the present invention and a corresponding spherical surface;

FIG. 13 schematically illustrates longitudinal aberration graphs of IOLs having three different posterior surface designs (namely, the posterior surface being an obviously convex spherical surface, a flat spherical surface and an obviously convex aspherical surface design) with a 5 mm light transmission aperture and 20D diopter as obtained through ZEMAX simulation in an eye model;

FIG. 14A is an aberration distribution diagram when a spherical surface IOL, a single Q-value aspherical surface IOL and a higher order aspherical surface IOL are at a central position (with a pupil diameter 5.0 mm);

FIG. 14B is an aberration distribution diagram when a spherical surface IOL, a single Q-value aspherical surface IOL and a higher order aspherical surface IOL off-center 1 mm (with a pupil diameter 5.0 mm);

FIG. 14C is an aberration distribution diagram when a spherical surface IOL, a single Q-value aspherical surface IOL and a higher order aspherical surface IOL are inclined 7° (with a pupil diameter 5.0 mm);

FIG. 15 is a modulation transfer function (MTF) graph as actually measured in a human eye model with a cornea aberration when a spherical surface IOL, a single Q-value aspherical surface IOL and a higher order aspherical surface IOL with a small radius of curvature at a posterior surface are at a central position (with a pupil diameter 5.0 mm);

FIG. 16 is a MTF graph as actually measured in a human eye model with a cornea aberration when a spherical surface IOL, a single Q-value aspherical surface IOL and a higher order aspherical surface IOL with a small radius of curvature at a posterior surface are off-centered 1 mm (with a pupil diameter 5.0 mm);

FIG. 17 is a MTF graph as actually measured in a human eye model with a cornea aberration when a spherical surface IOL, a single Q-value aspherical surface IOL and a higher order aspherical surface IOL with a small radius of curvature at a posterior surface are off-centered 0.5 mm and inclined 5° (with a pupil diameter 5.0 mm);

FIG. 18 schematically illustrates the principle of forming a toric surface;

FIG. 19A and FIG. 19B are respectively a point spread function contrast diagram after an ordinary aspherical surface intraocular lens and Toric intraocular lens of the present invention are respectively implanted into a human eye with corneal astigmatism obtained through simulation by adopting ZEMAX, wherein the human eye model has 2.9D corneal astigmatism;

FIG. 20A and FIG. 20B are respectively an MTF contrast diagram after an ordinary aspherical intraocular lens and Toric intraocular lens of the present invention are respectively implanted into a human eye with corneal astigmatism obtained through simulation by adopting ZEMAX, wherein the human eye model has 2.9D corneal astigmatism;

FIG. 21 schematically illustrates a perspective view of a one-piece posterior chamber intraocular lens according to another embodiment of the present invention, wherein haptics are unfolded and not yet folded onto the anterior surface of the optics of the intraocular lens, the view particularly including a cross section of a transition connection section between the optics and haptics;

FIG. 22 particularly and illustratively shows the transition connection section between the optics and the haptics in a one-piece posterior chamber intraocular lens as shown in the cross section of FIG. 21;

FIG. 23 schematically shows a positional relationship between an intraocular lens axial direction and a maximum refractive power direction of the human cornea when the Toric intraocular lens is implanted into a human eye;

FIG. 24 schematically shows a MTF contrast diagram of the intraocular lens (preferred embodiment) of the present invention with a spherical surface and a toric surface being respectively located on both sides and a prior-art intraocular lens (comparative example) with the aspherical surface and the toric surface being located on the same side, at a spatial frequency of 0-100 lp/mm in a human eye model with astigmatism and a pupil diameter 3.0 mm;

FIG. 25 schematically shows a wave front chart of a surface design of an intraocular lens of the present invention at an image surface in a human eye model (with an aspherical surface and a toric surface being respectively located on both sides); and FIG. 26 schematically a wave front chart of a surface design in the prior art in a human eye model with an aspherical surface and a toric surface being combined on one surface.

The same reference signs used in the figures of the present application denote identical or similar elements.

LISTING OF PARTS DENOTED BY REFERENCE SIGNS 1 posterior chamber intraocular lens
2 optic
3 effective optical area
4 effective optical area edge
5 haptics
6 effective optical area anterior surface
7 effective optical area posterior surface
8 longitudinal central plane of optics of the intraocular lens
8'-8' longitudinal center line of optics of the intraocular lens
9 posterior capsule
10 gap
11 cornea
12 capsule bag
13 fold gap
14 sharp bend
15 transition connection section
15'-15' longitudinal center line of the transition connection section
16 haptic root
16'-16' longitudinal center line of the haptic root
18 Toric IOL axial mark
A an intersection point of the longitudinal center line of the IOL optics and the longitudinal center line of the transition connection section
α haptic angle
β an inclination angle of the transition connection section
D-D' ocular axis direction
E-E' maximum refractive power direction of human cornea
d-d' rotation formation axis of a toric surface
O effective optical area (anterior or posterior) surface apex
R rotation radius
r radius of curvature

DETAILED DESCRIPTION OF PREFERRED EMBODIMENTS

The following specific embodiments are only used to further illustrate the present invention, but the present invention is not limited to the following specific embodiments. Any variations on the basis of these embodiments all fall within the scope of protection of the present invention so long as they conform to the principle, spirit and scope of the present invention.

(I) Backwardly Convex Design of the IOL Effective Optical Area

Further improvement of stability of the implanted IOL in the human eye capsule bag and reduction of the probability of posterior capsule opacification are factors to be considered first in design of the surface shape of the IOL effective optical area of the present invention.

Figure 1:
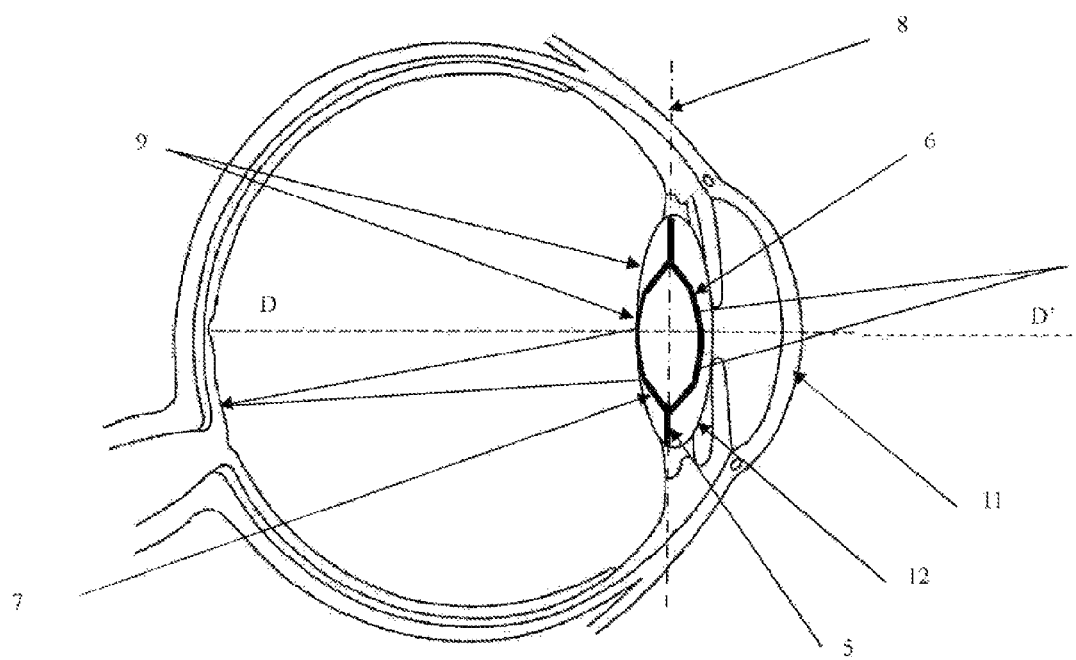
Figure 2:
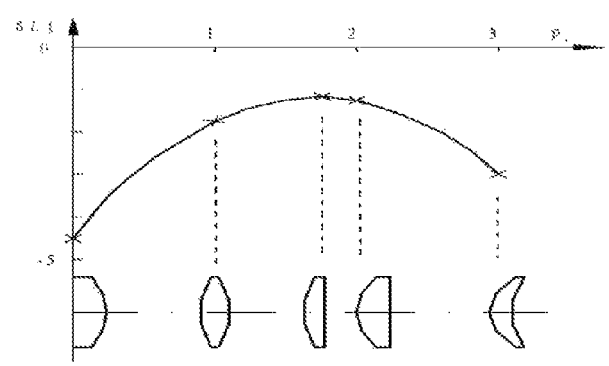
Figure 3:
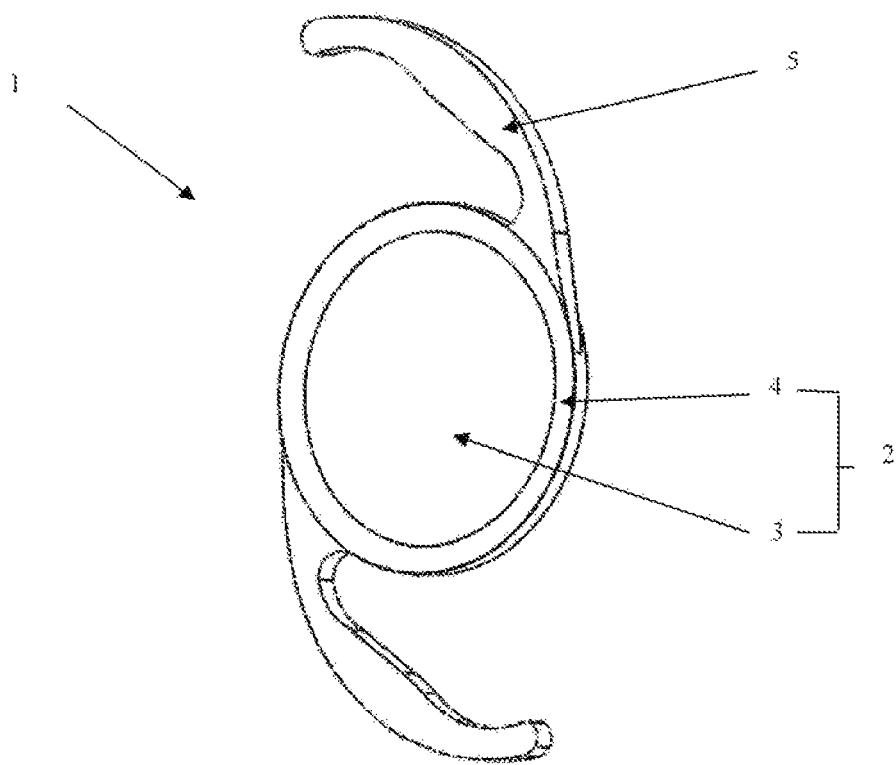
Figure 4:
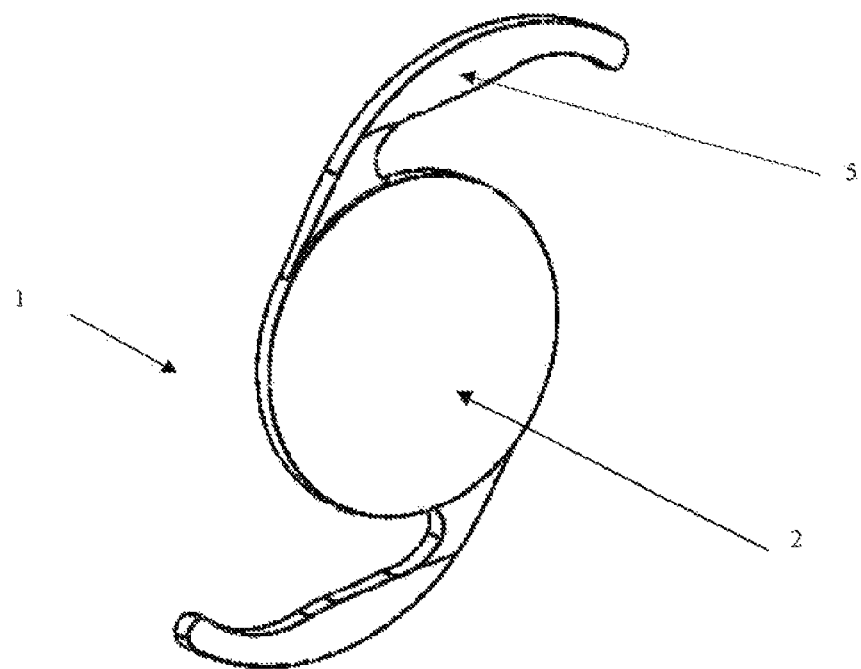

FIG. 3 is a perspective view of a one-piece posterior chamber intraocular lens 1 according to an embodiment of the present invention as viewed from above an anterior surface of the intraocular lens. FIG. 4 illustrates a perspective view of a one-piece posterior chamber intraocular lens according to an embodiment of the present invention as viewed from above a posterior surface of the intraocular lens. As shown in FIGS. 3 and 4, the posterior chamber IOL 1 comprises an optic 2 consisting of an effective optical area 3 and an effective optical area edge 4; and two support haptics 5 integrally formed with the optic 2. The support haptics 5 are directly connected to the effective optical area edge 4 of the optic. Certainly, those skilled in the art may appreciate that the number of haptics 5 may be more than two, preferably less than six. The haptics 5 are symmetrically disposed on the effective optical area edge 4 around a circumferential direction of the optic 2 and connected to the anterior surface of the optic. Certainly, those skilled in the art may appreciate that the haptics 5 are symmetrically disposed on the effective optical area edge 4 around a circumferential direction of the optic 2 and integrally connected to the side of the optic. As shown in FIG. 3 and FIG. 4, a posterior surface 7 of the effective optical area 3 is convex and an anterior surface 6 of the effective optical area 3 is convex. Those skilled in the art may appreciate that a surface shape of the posterior surface 7 of the effective optical area 3 may comprise one of spherical shape, aspherical surface, toric surface, multi-focal surface of multi-area refraction design and multi-focal surface of multi-area diffraction design; a surface shape of the anterior surface 6 of the effective optical area 3 comprises one of spherical shape, aspherical surface, toric surface, multi-focal surface of multi-area refraction design and multi-focal surface of multi-area diffraction design. As shown in FIG. 3 and FIG. 4, the haptics 5 of the one-piece posterior chamber IOL 1 are in a unfolded state and not yet folded onto the anterior surface of the IOL optic 2.

Figure 5:
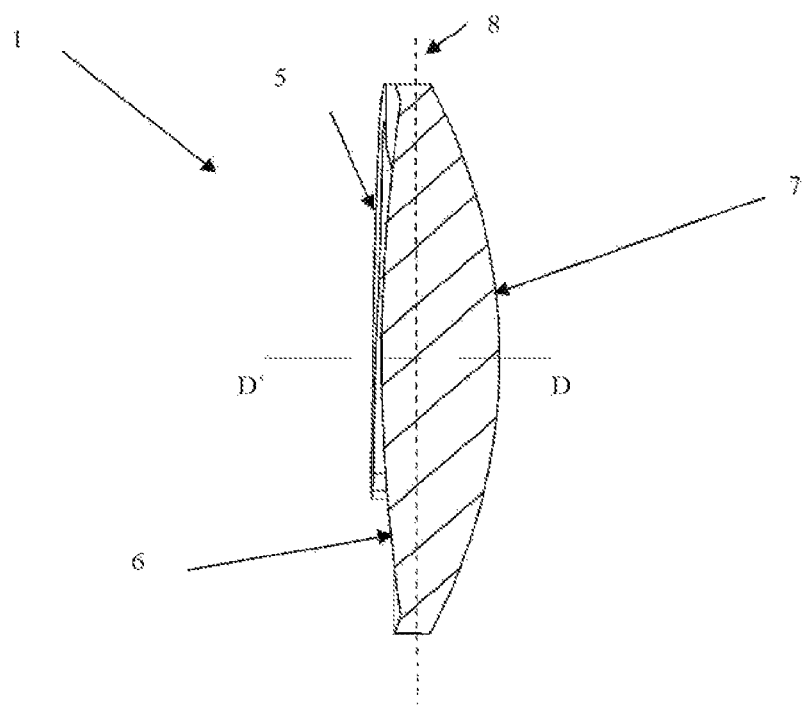
FIG. 5 illustrates a cross-sectional view of a one-piece e posterior chamber intraocular lens according to an embodiment of the present invention, wherein haptics are already folded onto the anterior surface of the optics of the intraocular lens.

FIG. 5 illustrates a cross-sectional view of a one-piece posterior chamber intraocular lens 1 according to an embodiment of the present invention, wherein haptics 5 are already folded onto the anterior surface of the optics 2 of the intraocular lens. As can be clearly seen from the figure, the effective optical area posterior surface 7 of the posterior chamber IOL 1 is more obviously convex than the effective optical area anterior surface 6 of the posterior chamber IOL 1. Particularly regarding the surface design of the posterior chamber IOL 1 with an obviously backwardly convex effective optical area posterior surface, the L-shaped or C-shaped haptics of the present invention can form a three-point stabilizing structure with the obviously backwardly convex posterior surface of the posterior chamber IOL 1 of the present invention, so as to improve stability of a position of the intraocular lens in a capsule bag and facilitate reduction of an incidence rate of posterior capsule opacification (PCO) after implantation of the intraocular lens.

FIG. 6 illustrates a schematic view of interaction relationship between an effective optical area posterior surface 7 and a posterior capsule 9 of a posterior chamber intraocular lens 1 in the prior art implanted into a human eye when a capsulate bag is in a retracted state. The surface shape of the effective optical area of the prior-art posterior chamber IOL 1 shown in FIG. 6 is a slightly convex surface shape (the effective optical area anterior surface is convex and the effective optical area posterior surface is slightly convex). After the prior-art posterior chamber IOL 1 shown in FIG. 6 is implanted into the human eye, the posterior chamber IOL 1 is maintained at a relative position in the human eye posterior chamber capsule bag by virtue of interaction between the support haptics 5 and the capsule bag 12. The retraction and expansion of the capsule bag act upon the support haptics 5, so that the IOL connected to the haptics is pressed or stretched to move forward and rearward along an ocular axis direction D-D'. Since the effective optical area posterior surface of the prior-art posterior chamber IOL 1 is slightly convex (or approximately flat), when the prior-art posterior chamber IOL 1 already implanted into the human eye is pressed or stretched in the posterior chamber, a gap 10 more or less exits between the effective optical area posterior surface and the posterior capsule membrane 9; upon retraction of the capsule bag, the prior-art posterior chamber IOL, under action of a retraction force P, may move in a larger space scope S, whereby the close contact between the effective optical area posterior surface 7 and the posterior capsule membrane 9 is caused unstable, and the residual lens epithelial cells after cataract surgery multiply and easily migrate to between the prior-art IOL effective optical area posterior surface and posterior capsule through the gap 10 between the effective optical area posterior surface and the human eye posterior capsule membrane 9, whereby posterior capsule opacification (PCO) phenomenon is likely to occur.

FIG. 7 illustrates a schematic view of interaction relationship between an effective optical area posterior surface 7 and a posterior capsule membrane 9 of a posterior chamber intraocular lens 1 according to the present invention implanted into a human eye when a capsulate bag is in a retracted state. As compared with the convexity of the effective optical area posterior surface of the prior-art posterior chamber IOL 1 as shown in FIG. 6, the effective optical area posterior surface of the posterior chamber IOL 1 of the present invention of FIG. 7 is more obviously outwardly convex. After the posterior chamber IOL 1 shown in FIG. 7 is implanted into the human eye, the posterior chamber IOL 1 is maintained at a relative position in the human eye posterior chamber capsule bag by virtue of interaction between the support haptics 5 and the capsule bag. The retraction and expansion of the capsule bag act upon the support haptics 5, so that the IOL 1 connected to the haptics 5 is pressed or stretched to move forward and rearward along an ocular axis direction D-D'. As compared with the commonly-seen the prior-art IOL, there is a smaller gap between the effective optical area posterior surface and the posterior capsule of the IOL with an obviously rearwardly convex surface shape of the present invention shown in FIG. 7, and upon retraction of the capsule bag, the posterior chamber IOL, under action of a retraction force P, may move in a relatively smaller space scope S, whereby stability of the position of the lens in the capsule bag is improved. Specifically, since the effective optical area posterior surface of the IOL 1 of the present invention as shown in FIG. 7 is obviously outwardly convex, when the IOL 1 is implanted into the human eye and pressed or stretched in the posterior chamber, the gap 10 between the effective optical area posterior surface of the posterior chamber IOL 1 of the present invention and the human eye posterior capsule membrane 9 is minimized so that the effective optical area posterior surface can more closely contact with the human eye capsule membrane 9, thereby making the close contact between the effective optical area posterior surface 7 and the posterior capsule membrane 9 stabler, and prevent the residual lens epithelial cells after cataract surgery from multiplying and from migrating to between the prior-art IOL effective optical area posterior surface and posterior capsule through the gap 10 between the effective optical area posterior surface and the human eye posterior capsule membrane 9. As can be seen from the above, the obviously convex posterior surface of the effective optical area of the IOL may reduce the gap between the posterior capsule and the effective optical area and reduce an incidence rate of posterior capsule opacification (PCO) after implantation of the IOL.

FIG. 8 illustrates interaction relationship between an effective optical area posterior surface and a posterior capsule membrane of a posterior chamber intraocular lens in the prior art as shown in circle G of FIG. 6. FIG. 9 illustrates interaction relationship between an effective optical area posterior surface and a posterior capsule membrane of a one-piece posterior chamber intraocular lens in the present invention as shown in circle H of FIG. 7. A premise for the right-angle design adopted by the prior-art IOL effective optical area edge 4 to prevent growth of the PCO is that the IOL edge right-angle side can press tightly against the posterior capsule membrane 9 and thereby better hinders the migrational flow of the lens epithelial cells. A comparison of FIG. 8 and FIG. 9 shows: as compared with the prior-art posterior chamber IOL, the effective optical area of posterior surface of the posterior chamber IOL of the present invention can more closely contact with the posterior capsule membrane, whereby the obviously convex surface shape design of the posterior surface of the posterior chamber IOL effective optical area of the present invention can give full play to the advantages of the right-angle edge effect of the IOL optical effective area edge.

Upon implantation of the IOL, the IOL needs to be placed in a guide-in head for surgery, and a haptic-folding act is usually performed. FIG. 10 illustrates, in the form of a cross sectional view, a situation in which haptics of one-piece posterior chamber intraocular lens in the prior art are folded onto the effective optical area anterior surface before the intraocular lens is implanted into a human eye. FIG. 11 illustrates, in the form of a cross sectional view, a situation in which haptics of one-piece posterior chamber intraocular lens in the present invention are folded onto the effective optical area anterior surface before the intraocular lens is implanted into a human eye. Before implantation, the haptics of a one-piece IOL generally need to be folded onto the anterior surface 6 of the IOL optic so as to prevent a thimble of an implanter from damaging the haptics 5 before advancing the IOL. A comparison of FIG. 10 and FIG. 11 makes the following noticeable: if the anterior surface of the IOL effective optical area is too convex, the haptics gets close to the anterior surface of the IOL effective optical area so that a fold space 13 is smaller. When the IOL is pushed out of the guide-in head, the haptics 5 cannot be easily unfolded. The obviously convex surface shape design of the effective optical area posterior surface 7 of the one-piece posterior chamber IOL 1 of the present invention is such that the anterior surface 6 of the optic may be relatively flatter so as to reduce the contact area and action force between the folded haptics and the anterior surface 6 of the optic to make the fold gap 13 larger. Therefore, the obviously convex surface shape design of the effective optical area posterior surface 7 of the one-piece posterior chamber IOL 1 of the present invention is further such that after the one-piece posterior chamber IOL 1 of the present invention is implanted into the human eye, the haptics folded onto the anterior surface 6 of the optic of the one-piece posterior chamber IOL 1 of the present invention can be more easily unfolded and thereby reduces the risk of failure to smoothly unfold due to mutual adhesion of the support haptics and the IOL effective optical areal.

FIG. 21 illustrates a perspective view of a one-piece posterior chamber intraocular lens according to another embodiment of the present invention, wherein haptics are unfolded and not yet folded onto the anterior surface of the effective optical lens of the intraocular lens, the view particularly including a cross section of a transition connection section between the optics and haptics. FIG. 22 specifically and illustratively shows the transition connection section between the optics and the haptics in a one-piece posterior chamber intraocular lens as shown in the cross section of FIG. 21. As shown in FIG. 21 and FIG. 22, the posterior chamber IOL 1 according to another embodiment of the present invention comprises: an optic 2 consisting of an effective optical area 3 and an effective optical area edge 4, two support haptics 5 integrally formed with the optic 2, and a transition connection section 15 between the optic 2 and the support haptics 5. The support haptics 5 are directly connected to the effective optical area edge 4 of the optic 2 via the transition connection section 15. The transition connection section 15 is substantially conical or cylindrical and is machined during preparation of the IOL. Alternatively, the effective optical area edge 4 may further comprise a sharp bend 14 such as a right-angle side configuration. One end of the transition connection section 15 is directly connected to the effective optical area edge 4 of the optic 2, and the other end of the transition connection section 15 is directly connected to haptic roots 16 of the support haptics 5. The haptic roots 16 are located at an end opposite to a free end of the support haptics 5 and substantially extend straight. A longitudinal center line 16'-16' of the haptic roots 16 is inclined relative to a longitudinal center line 8'-8' of the optic 2 of the posterior chamber IOL 1, and is at a haptic angle α in a range of 0°-7°. A longitudinal center line 15'-15' of the transition connection section 15 is inclined relative to the longitudinal center line 8'-8' of the optic 2 of the posterior chamber IOL 1, and is at a transition connection section inclination angle β in a range of 10°-45°. The transition connection section inclination angle β is greater than the haptic shaping angle α. The sharp bend 14 facilitates forming a mechanical barrier on the posterior capsule membrane 9, interrupting migrational flow of the epithelial cells and meanwhile enhancing connection strength of the optic and the haptics. Besides, when the IOL 1 connected to the support haptics 5 is pressed or stretched due to retraction and expansion of the capsule bag, due to existence of the haptic shaping angle α (namely, a design angle of haptics), a radial force received by the haptics 5 is divided into a component force in the ocular axis direction enabling the optical surface to move towards the posterior capsule and a component force perpendicular to the ocular axis direction enabling the surface shape of the effective optical area to change, so as to ensure permanent close contact between the effective optical area posterior surface 7 and the posterior capsule 9. This close contact type structural design substantially reduces occurrence probability of PCO. The structural configuration including the haptic shaping angle α, the transition connection section 15 and (optionally) the sharp bend 14 is combined with the obviously rearwardly convex effective optical area posterior surface 7 of the posterior chamber IOL 1 of the present invention so that the obviously rearwardly convex effective optical area posterior surface 7 can be allowed to more closely contact with the posterior capsule membrane 9 such that the posterior chamber IOL 1 of the present invention can be more firmly positioned in the posterior capsule 9, thereby better blocking growth of PCO. Certainly, those skilled in the art may appreciate that the number of haptics 5 may be more than two, preferably less than six. The haptics 5 are symmetrically disposed on the effective optical area edge 4 around a circumferential direction of the optic 2 and connected to the anterior surface of the optic. Certainly, those skilled in the art may appreciate that the haptics 5 are symmetrically disposed on the effective optical area edge 4 around a circumferential direction of the optic 2 and integrally connected to the side of the optic.

In addition, those skilled in the art can further appreciate that the posterior chamber IOL with obviously convex effective optical area posterior surface may be the one-piece IOL as described in the above embodiments, or three-piece IOL. Regarding the three-piece IOL, surface shape design features of the effective optical area thereof are similar to those of the one-piece IOL as described in the above embodiments and will not be detailed here. As compared with the posterior chamber IOL in the prior art, the three-piece e posterior chamber IOL according to the present invention has the obviously convex effective optical area posterior surface, which can reduce the gap between the posterior capsule and the effective optical area after implantation, reduce the opportunity for the epithelial cells to migrate to between the three-piece IOL posterior surface and posterior capsule and thereby reduce incidence rate of PCO after implantation of the three-piece posterior chamber IOL. Besides, the obviously convex effective optical area posterior surface of the three-piece posterior chamber IOL according to the present invention can also more closely contact with the posterior capsule membrane so that the IOL can be more stably positioned in the posterior capsule and thereby advantages of the right-angle edge effect of the IOL effective optical area edge are reflected better.

(II) The Surface Shape Design of the IOL Effective Optical Area

Table 2 below lists an example of surface shape design of the effective optical area of the posterior chamber IOL of the present invention fabricated from different materials.

When the effective optical area surface of the posterior chamber IOL of the present invention has a spherical surface shape, the surface shape of the effective optical area surface of the posterior chamber IOL of the present invention can be directly represented by using the radii of curvature of the IOL anterior and posterior effective optical area surfaces.

When the effective optical area surface of the posterior chamber IOL of the present invention further adopts high order aspherical surface design and/or toric surface design, this means adding the high order aspherical surface design and/or toric surface design on the basic spherical surface of the effective optical area of the posterior chamber IOL adopting different materials as listed in the following Table 2 in the present invention. At this time, the radius of curvature of the anterior surface and the radius of curvature of the posterior surface as listed in the following Table 2 are respectively the radius of curvature of the basic spherical surface of the effective optical area anterior surface of the posterior chamber IOL and the radius of curvature of the basic spherical surface of the effective optical area posterior surface of the posterior chamber IOL. An aspherical surface design is intended to further improve the imaging quality of the basic spherical surface, and the toric surface design (Toric) is intended to additionally correct human eye astigmatism and improve visual quality of astigmatism sufferer.

For the sake of convenient and consistent depictions, the spherical surfaces involved by the posterior chamber IOL of the present invention in the above two situations are both called "basic spherical surface" in further explanations and analysis of data in the following Table 2.

The refractive indices of examples of the following materials adopted by the posterior chamber IOL of the present invention all are between 1.45 and 1.56. As known by those skilled in the art, a conventional preparation method may be adopted according to needs to enable the prepared materials to have any refractive index between 1.45 and 1.56. Besides, a thickness at a center of the effective optical area of the posterior chamber IOL of the present invention is in a range of 0.3 mm-1.2 mm, and a thickness of the effective optical area edge is in a range of 0.3 mm-0.6 mm. "A thickness at a center of the effective optical area" refers to a thickness at the thickest position at the center of the effective optical area of the posterior chamber IOL of the present invention; "a thickness of the effective optical area edge" refers to a thickness measured at a transition position between the effective optical area and the effective optical area edge of the posterior chamber IOL of the present invention. As publicly known by those skilled in the art, the magnitude of the thickness at a center of the effective optical area of the posterior chamber IOL of the present invention and the magnitude of the thickness of the effective optical area edge of the posterior chamber IOL of the present invention depend on the utilized material and the achieved diopter. These IOLs of the present invention having the surface shape designs of the effective optical area surface as listed in Table 2 all can achieve a diopter of 5.0D-36.0D. At present, the most frequently and clinically used IOL is an IOL having a diopter approximate to 20D.

TABLE 2

Example of Surface Shape Design of Effective Optical Area of Posterior Chamber IOL of the Present Invention

| example | Material | Refractive index | Diopter (D) | Radius of curvature of anterior surface (mm) | Radius of curvature of posterior surface (mm) | Radius of curvature of posterior surface/Radius of curvature of anterior surface |
|---|---|---|---|---|---|---|
| 1 | Silicone/hydrogel | 1.46 | 5.0 | 48.6 | 48.0 | 98.8% |
|   |   |   | 6.0 | 48.5 | 35.0 | 72.2% |
|   |   |   | 9.0 | 26.5 | 13.0 | 49.1% |
|   |   |   | 15.0 | 44.5 | 10.0 | 22.7% |
|   |   |   | 20.0 | 25.6 | 8.0 | 31.3% |
|   |   |   | 26.5 | 12.0 | 7.5 | 62.5% |
|   |   |   | 30.0 | 9.2 | 7.3 | 79.3% |
|   |   |   | 36.0 | 7.1 | 6.6 | 92.9% |
| 2 | hydrophobic acrylate | 1.47 | 5.0 | 52.5 | 52.0 | 99.0% |
|   |   |   | 6.0 | 59.0 | 35.0 | 59.3% |
|   |   |   | 9.0 | 25.5 | 15.0 | 58.8% |
|   |   |   | 15.0 | 44.5 | 11.0 | 24.7% |
|   |   |   | 20.0 | 28.7 | 8.5 | 29.6% |
|   |   |   | 26.5 | 17.0 | 7.0 | 41.2% |
|   |   |   | 30.0 | 11.0 | 7.3 | 66.4% |
|   |   |   | 36.0 | 7.8 | 7.0 | 89.7% |
| 3 | hydrophobic acrylate | 1.48 | 5.0 | 55.1 | 55.0 | 99.8% |
|   |   |   | 6.0 | 47.1 | 45.5 | 96.6% |
|   |   |   | 9.0 | 74.0 | 19.5 | 26.4% |
|   |   |   | 15.0 | 55.7 | 11.1 | 20.0% |
|   |   |   | 20.0 | 18.5 | 11.1 | 60.0% |
|   |   |   | 26.5 | 14.7 | 8.1 | 55.5% |
|   |   |   | 30.0 | 10.7 | 8.1 | 75.7% |
|   |   |   | 36.0 | 8.0 | 7.5 | 93.7% |
| 4 | polymethyl methacrylate (PMMA) | 1.49 | 5.0 | 60.0 | 59.5 | 99.2% |
|   |   |   | 6.0 | 56.0 | 45.5 | 81.2% |
|   |   |   | 9.0 | 30.0 | 17.0 | 56.7% |
|   |   |   | 15.0 | 44.5 | 13.1 | 29.4% |
|   |   |   | 20.0 | 44.7 | 9.0 | 20.1% |
|   |   |   | 26.5 | 29.5 | 7.0 | 23.7% |
|   |   |   | 30.0 | 17.2 | 7.0 | 40.7% |
|   |   |   | 36.0 | 10.9 | 6.8 | 62.4% |
| 5 | hydrophobic acrylate | 1.51 | 5.0 | 67.0 | 66.0 | 98.5% |
|   |   |   | 6.0 | 74.0 | 45.5 | 61.5% |
|   |   |   | 9.0 | 65.5 | 14.9 | 22.7% |
|   |   |   | 15.0 | 44.5 | 15.3 | 33.6% |
|   |   |   | 20.0 | 55.5 | 9.9 | 17.8% |
|   |   |   | 26.5 | 53.5 | 7.2 | 13.5% |
|   |   |   | 30.0 | 27.5 | 7.0 | 25.5% |
|   |   |   | 36.0 | 14.4 | 7.0 | 48.6% |
| 6 | hydrophobic acrylate | 1.52 | 5.0 | 71.0 | 70.0 | 98.6% |
|   |   |   | 6.0 | 73.0 | 50.0 | 68.5% |
|   |   |   | 9.0 | 55.0 | 16.6 | 30.2% |
|   |   |   | 15.0 | 44.5 | 16.5 | 37.1% |
|   |   |   | 20.0 | 55.5 | 10.6 | 19.1% |
|   |   |   | 26.5 | 55.5 | 7.6 | 13.7% |
|   |   |   | 30.0 | 37.0 | 7.0 | 18.9% |
|   |   |   | 36.0 | 17.0 | 7.0 | 41.2% |
| 7 | hydrophobic acrylate | 1.55 | 5.0 | 81.0 | 80.0 | 98.8% |
|   |   |   | 6.0 | 84.0 | 57.0 | 67.9% |
|   |   |   | 9.0 | 58.0 | 20.0 | 34.5% |
|   |   |   | 15.0 | 44.5 | 20.3 | 45.6% |
|   |   |   | 20.0 | 55.0 | 12.7 | 23.1% |
|   |   |   | 26.5 | 55.5 | 9.0 | 16.4% |

TABLE 2-continued

Example of Surface Shape Design of Effective Optical Area
of Posterior Chamber IOL of the Present Invention

| example | Material | Refractive index | Diopter (D) | Radius of curvature of anterior surface (mm) | Radius of curvature of posterior surface (mm) | Radius of curvature of posterior surface/Radius of curvature of anterior surface |
|---|---|---|---|---|---|---|
| | | | 30.0 | 53.0 | 7.8 | 14.7% |
| | | | 36.0 | 30.8 | 7.0 | 22.7% |

As can be seen from Table 2, the radius of curvature of the basic spherical surface of the posterior surface of the effective optical area of the posterior chamber IOL of the present invention is substantially in a range of 6.6 mm-80.0 mm. The radius of curvature of the basic spherical surface of the anterior surface of the effective optical area of the posterior chamber IOL of the present invention is substantially in a range of 7.1 mm-84.0 mm.

In Example 1, in another preferred embodiment of the present invention, the posterior chamber IOL is made of silicone or hydrogel with a refractive index 1.46, for example, the material was once used to prepare SI40NB silicone IOL of AMO Inc. of the United State and Akreos hydrogel IOL of Bausch & Lomb Incorporated. As can be seen from Table 2, the radius of curvature of the posterior surface of the effective optical area of the posterior chamber IOL is substantially in a range of 6.6 mm-48.0 mm, and the radius of curvature of the anterior surface of the effective optical area of the posterior chamber IOL is substantially in a range of 7.1 mm-48.6 mm. To better achieve the above advantageous effect of the present invention, the radius of curvature of the posterior surface of the effective optical area is preferably in a range of 7.5 mm-10.0 mm, or more preferably about 8.0 mm.

In Example 2, the posterior chamber IOL is made of hydrophobic acrylate with a refractive index 1.47, for example, the material was once used to prepare AR40e IOL of AMO Inc. of the United State. As can be seen from Table 2, the radius of curvature of the posterior surface of the effective optical area of the posterior chamber IOL is in a range of 7.0 mm-52.0 mm, and the radius of curvature of the anterior surface of the effective optical area of the posterior chamber IOL is in a range of 7.8 mm-59.0 mm. To better achieve the above advantageous effect of the present invention, the radius of curvature of the posterior surface of the effective optical area is preferably in a range of 7.0 mm-11.0 mm, or more preferably about 8.5 mm.

In Example 3, the posterior chamber IOL is made of hydrophobic acrylate which is available from Eyebright Medical Technology (Beijing) Co., Ltd. As can be seen from Table 2, the material for the posterior chamber IOL has a refractive index 1.48. The radius of curvature of the posterior surface of the effective optical area of the posterior chamber IOL is in a range of 7.5 mm-55.0 mm, and the radius of curvature of the anterior surface of the effective optical area of the posterior chamber IOL is in a range of 8.0 mm-74.0 mm. To better achieve the above advantageous effect of the present invention, the radius of curvature of the posterior surface of the effective optical area is preferably in a range of 8.1 mm-19.5 mm, or more preferably about 11.1 mm.

In Example 4, the posterior chamber IOL is made of polymethyl methacrylate (PMMA) which is a commonly-used material for preparing the IOL in the early stage. As can be seen from Table 2, the material for the posterior chamber IOL has a refractive index 1.49. The radius of curvature of the posterior surface of the effective optical area of the posterior chamber IOL is in a range of 6.8 mm-59.5 mm, and the radius of curvature of the anterior surface of the effective optical area of the posterior chamber IOL is in a range of 10.9 mm-60.0 mm. To better achieve the above advantageous effect of the present invention, the radius of curvature of the posterior surface of the effective optical area is preferably in a range of 7.0 mm-13.1 mm, or more preferably about 9.0 mm.

In Example 5, the posterior chamber IOL is made of hydrophobic acrylate with a refractive index 1.51, and for example this material was once used by HOYA CORPORATION to prepare AF-1 model IOL. As can be seen from Table 2, the radius of curvature of the posterior surface of the effective optical area of the posterior chamber IOL is in a range of 7.0 mm-66.0 mm, and the radius of curvature of the anterior surface of the effective optical area of the posterior chamber IOL is in a range of 14.4 mm-74.0 mm. To better achieve the above advantageous effect of the present invention, the radius of curvature of the posterior surface of the effective optical area is preferably in a range of 7.2 mm-15.3 mm, or more preferably about 9.9 mm.

In Example 6, the posterior chamber IOL is made of hydrophobic acrylate which is available from Eyebright Medical Technology (Beijing) Co., Ltd. As can be seen from Table 2, the material for the posterior chamber IOL has a refractive index 1.52. The radius of curvature of the posterior surface of the effective optical area of the posterior chamber IOL is in a range of 7.0 mm-70.0 mm, and the radius of curvature of the anterior surface of the effective optical area of the posterior chamber IOL is in a range of 17.0 mm-73.0 mm. To better achieve the above advantageous effect of the present invention, the radius of curvature of the posterior surface of the effective optical area is preferably in a range of 7.6 mm-16.5 mm, or more preferably about 10.6 mm.

In Example 7, the posterior chamber IOL is made of hydrophobic acrylate with a refractive index 1.55, for example, the material was once used by ALCON CORPORATION of the United State to prepare Acrys of series IOLs. As can be seen from Table 2, the radius of curvature of the posterior surface of the effective optical area of the posterior chamber IOL is in a range of 7.0 mm-80.0 mm, and the radius of curvature of the anterior surface of the effective optical area of the posterior chamber IOL is in a range of 30.8 mm-84.0 mm. To better achieve the above advantageous effect of the present invention, the radius of curvature of the posterior surface of the effective optical area is preferably in a range of 9.0 mm-20.3 mm, or more preferably about 12.7 mm.

Besides, as further can be seen from Table 2, the radius of curvature of the posterior surface of the effective optical area of the posterior chamber IOL is smaller than that of the anterior surface of the effective optical area. To better achieve the above advantageous effect of the present invention, the radius of curvature of the posterior surface of the effective optical area is 17.8%-60.0% of the radius of curvature of the anterior surface of the effective optical area; more preferably, the radius of curvature of the posterior surface of the effective optical area is 20.0%-45.6% of the radius of curvature of the anterior surface of the effective optical area.

Certainly, those skilled in the art, upon viewing Table 2, can appreciate that the radius of curvature of the posterior surface of the effective optical area of the posterior chamber IOL is substantially equal to that of the anterior surface of the effective optical area.

(II.1) A High Order Aspherical Surface Design of the IOL Effective Optical Area

In order to eliminate or reduce high order aberration (including spherical aberration and comatic aberration) of the prior-art IOL products to improve imaging quality, the effective optical area posterior surface or anterior surface of the obviously rearwardly convex posterior chamber IOL according to an embodiment of the present invention adopts a high order aspherical surface design and does not adopt a conventional single Q-value aspherical surface design (the single Q-value aspherical surface design can only complement spherical aberration).

A complementation principle of the aspherical surface of the effective optical area of the obviously rearwardly convex posterior chamber IOL of the present invention is that extra spherical aberration generated by the aspherical surface offsets the spherical aberration generated by the basic spherical surface, and the extra comatic aberration generated by the aspherical surface offsets the comatic aberration generated by the basic spherical surface.

In the present application, the high order aspherical surface design utilizes various variables upon designing a plural high order equation coefficient, and the resultant aspherical surface shape is more complicated than the basic spherical surface shape. The high order aspherical surface design can not only correct the spherical aberration but also correct high order aberration of other types, and reduce the lens's sensitivity to the implantation site.

To more accurately describe the surface shape of the effective optical area of the IOL of the present invention, a two-dimensional coordinate system is established with an effective optical area surface apex adopting a higher order aspherical surface design in the obviously rearwardly convex posterior chamber IOL as an original point, a longitudinal coordinate axis Y of the coordinate system is tangential with the effective optical area surface and passes through the effective optical area surface apex O; a horizontal coordinate axis Z of the coordinate system is parallel to an ocular axis direction D-D' and is at an angle of 90 degrees relative to the longitudinal coordinate axis Y and passes through the effective optical area surface apex O as shown in FIG. 5. Points on the effective optical area surface adopting the high order aspherical surface design in the obviously rearwardly convex posterior chamber IOL of the present invention are in rotational symmetrical relationship with the horizontal coordinate axis Z which passes through the effective optical area surface apex O and is parallel to an ocular axis direction D-D' as shown in FIG. 5. Therefore, the surface shape of the effective optical area surface adopting the high order aspherical surface design in the obviously rearwardly convex posterior chamber IOL of the present invention can be restored through rotational symmetrical conversion on the premise of defining the coordination relationship of the effective optical area surface adopting the high order aspherical surface design in the obviously rearwardly convex posterior chamber IOL of the present invention on a plane constituted by the longitudinal coordinate axis Y and the horizontal coordinate axis Z. Respective points on the effective optical area surface adopting the high order aspherical surface design in the obviously rearwardly convex posterior chamber IOL of the present invention on the plane constituted by the longitudinal coordinate axis Y and the horizontal coordinate axis Z may be represented as (Z, y). As shown in FIG. 12, $Z_{asph}$ is a Z value of any point of the aspherical surface shape on a curve on the two-dimensional coordination system plane YZ, and $Z_{sph}$ is a Z value Z of the spherical surface shape on a curve on the two-dimensional coordination system plane YZ.

Referring to FIG. 10, a curve of the aspherical surface of the obviously rearwardly convex posterior chamber IOL of the present invention on the two-dimensional coordinate system plane YZ satisfies the following expression of higher order aspherical surface design:

$$Z(y) = \frac{cy^2}{1+\sqrt{1-c^2y^2}} + \sum_{i=m}^{n} A_{2i} \cdot y^{2i} \quad (4)$$

Wherein Z(y) is an expression of the curve of the aspherical surface of the IOL effective optical area on the YZ plane, c is a reciprocal of a radius of curvature of the surface of the basic spherical surface of the effective optical area, y is a vertical distance of any point on the curve from the horizontal coordinate axis Z, $A_{2i}$ is a higher-order term coefficient of the aspherical surface, m, n are both an integer greater than or equal to 1 and n≥m, these terms reflect the magnitude of difference between the aspherical surface shape and the basic spherical surface shape. It can be seen from the above equation that the higher order aspherical surface can be considered as a superposition of the basic spherical surface term $$\frac{cy^2}{1+\sqrt{1-c^2y^2}}$$

and a deviation quantity, wherein the aspherical surface higher order coefficient $$\sum_{i=m}^{n} A_{2i} \cdot y^{2i}$$

is a superposed term.

Points on the convex aspherical surface shape are obtained in a way that the curve rotates around the horizontal coordinate axis (Z) for symmetry variation.

Table 3 lists parameter values $A_{2i}$ (m=2 and n=5) of superposed terms in equation (4) after increasing the higher order aspherical surface design on various Table 2-listed basic spherical surfaces of the IOL effective optical area according to a plurality of preferred embodiments of the present invention. The higher order coefficient in Table 2 is obtained through ZEMAX simulation, the human eye model adopted by the simulation is Liou eye model, and optimization is performed to allow a desired lens to have a better imaging quality in the case of off-centering 0.5 mm and inclining 5°.

Those skilled in the art should appreciate that the higher order coefficients in the superposed terms of the equation (4) will vary with different human eye models used.

a relatively flat posterior surface, which conforms to the minimization design principle of aberration (the minimization of the aberration is achieved by wholly curving surface shapes of two surfaces of the IOL), and has a smaller aberration (as shown by the dotted line in the figure); a spherical surface IOL with a small radius of curvature of the posterior surface has an obviously convex posterior surface,

TABLE 3

Parameter values (m = 2 and n = 5) of superposed terms of the aspherical surface shape expression of the present invention after increasing the higher order aspherical surface design on various basic spherical surfaces of the IOL effective optical area posterior surface

| Material | Refractive index | $A_4$ | $A_6$ | $A_8$ | $A_{10}$ |
|---|---|---|---|---|---|
| Silicone or hydrogel | 1.45 | −3.249E−003 | 2.182E−003 | −4.227E−004 | 3.113E−005 |
| Silicone or hydrogel | 1.46 | −2.804E−003 | 1.860E−003 | −3.201E−004 | 1.876E−005 |
| Hydrophobic acrylate | 1.47 | −1.776E−003 | 1.302E−003 | −2.294E−004 | 1.590E−005 |
| Hydrophobic acrylate (the present invention) | 1.48 | 2.431E−004 | 2.897E−004 | −5.417E−005 | 2.940E−006 |
| Hydrophobic acrylate | 1.48 | −1.518E−003 | 1.140E−003 | −2.503E−004 | 2.406E−005 |
| polymethyl methacrylate (PMMA) | 1.49 | −1.198E−003 | 8.292E−004 | −9.372E−005 | 1.303E−006 |
| Hydrophobic acrylate | 1.51 | −4.661E−004 | 3.294E−004 | 2.288E−005 | −8.575E−006 |
| Hydrophobic acrylate | 1.52 | −5.663E−004 | 3.534E−004 | 1.301E−005 | −7.467E−006 |
| Hydrophobic acrylate | 1.55 | −1.566E−003 | 1.069E−003 | −1.667E−004 | 8.009E−006 |
| Hydrophobic acrylate | 1.56 | 1.128E−003 | −6.244E−004 | 2.149E−004 | −2.196E−005 |

In addition, those skilled in the art can appreciate that if the aspherical surface design is added to the basic aspherical surface of the IOL effective optical area anterior surface, the higher order aspherical coefficients thereof are in an positive-negative opposite relationship with the corresponding higher order aspherical surface coefficients listed in Table 2. Those skilled in the art can also appreciate that the imaging quality will not be affected when the aspherical surface design is added to any one of the anterior surface and posterior surface of the IOL effective optical area.

As compared with the prior-art IOL adopting a spherical surface design and a prior-art IOL adopting a single Q-value aspherical surface design, the obviously rearwardly convex posterior chamber IOL with an effective optical area adopting the aspherical surface design according to the preferred embodiment of the present invention further improves the imaging quality of the IOL, as shown in FIGS. 13-17.

FIG. 13 shows longitudinal aberration graphs of IOL adopting three different posterior surface designs (spherical surface design with obviously convex posterior surface, spherical surface design with a flat posterior surface and aspherical surface design with obviously convex posterior surface) with a 5 mm light transmission aperture and a 20D diopter in a human eye model. The horizontal coordinate represents different aperture positions (represented by a percentage of aperture size), and the longitudinal coordinate represents the magnitude of the longitudinal aberration. As for an IOL at a central position, the longitudinal aberration is chiefly the spherical aberration. A spherical surface IOL with a larger radius of curvature of the posterior surface has and has an obviously increased aberration (as shown by the thin solid line) as compared with the spherical surface IOL with a flat posterior surface. One of surfaces of the IOL adopts an aspherical surface design, can effectively compensate aberration caused by the surface shape and obviously reduce the aberration (as shown by the thick solid line).

FIG. 14A, FIG. 14B and FIG. 14C respectively show higher order aberration distribution diagrams (with a pupil diameter of 5.0 mm) when a spherical surface IOL, a single Q-value aspherical surface IOL and a higher order aspherical surface IOL are in a central position, a off-centered state and an inclined state respectively. When the IOL is at the central position in the human eye capsule bag, the spherical surface IOL has a larger aberration, the single Q-value aspherical surface may correct aberration and does not involve other higher order aberrations (or involves a very small higher order aberration), the higher order aspherical surface may also correct the aberration but has a slightly larger surplus aberration than the single Q-value aspherical value. When the IOL is in a off-centered or inclined state in the human eye capsule bag, the spherical surface and aspherical surface both have the spherical aberration and the comatic aberration, but the single Q-value aspherical surface generates the largest comatic aberration. The higher order aspherical surface generates a smaller comatic aberration than the single Q value, and has a higher order aberration generally smaller than the spherical surface and the single Q-value aspherical surface.

In this art, for either the large higher order aberration system or smaller higher order aberration system, MTF graph is an effective, objective and full image quality evaluating method. In the practical sense, a MTF value represents contrast and sharpness of an optical image, is measured by how many lines are presented in a one-millimeter scope, and has a measure unit lp/mm.

FIG. 15 is a modulation transfer function (MTF) graph as actually measured in a human eye model with a cornea aberration when a spherical surface IOL, a single Q-value aspherical surface IOL and a higher order aspherical surface IOL with a small radius of curvature at a posterior surface are at a central position (with a pupil diameter 5.0 mm). As can be seen from the figure, the spherical surface IOL at the central position has a larger spherical aberration, with the MTF curve lower; and the single Q-value aspherical surface IOL and the IOL of the present invention both can correct the spherical aberration very well.

FIG. 16 is a MTF graph as actually measured in a human eye model with a cornea aberration when a spherical surface IOL, a single Q-value aspherical surface IOL and a higher order aspherical surface IOL with a small radius of curvature at a posterior surface are off-centered 1 mm in the human eye capsule bag (with a pupil diameter 5.0 mm). As can be seen from the figure, when being off-centered 1 mm in the human eye capsule bag, the IOL of the present invention is apparently advantageous than other types of IOLs in medium and low frequency bands, particularly below 50 lp/mm (50 lp/mm indicates 0.5 vision), but not distinct from other types of IOLs at the high frequency bands. Generally speaking, the IOL of the present invention is rather advantageous than the remaining types of IOLs.

FIG. 17 is a MTF graph as actually measured in a human eye model with a cornea aberration when a spherical surface IOL, a single Q-value aspherical surface IOL and a higher order aspherical surface IOL with a small radius of curvature at a posterior surface are off-centered 0.5 mm and inclined 5° (with a pupil diameter 5.0 mm). It can be seen from the figure that upon off-centering and inclination at the same time, the IOL of the present invention is obviously advantageous and exhibits excellent optical performance at the 100 lp/mm full frequency band.

It can be seen from the above figures that the obviously rearwardly convex posterior chamber IOL adopting the aspherical surface design according to a preferred embodiment of the present invention solves the problem that the lens surplus aberration is larger than the ordinary surface shape design because the radius of curvature of the IOL posterior surface is smaller than that of the anterior surface and solves the problem that the ordinary aspherical surface (single Q-value aspherical surface) IOL is too sensitive to disalignment of implantation (off-centering and inclination occurring during the surgery).

To conclude, the present invention belongs to the field of design of the effective optical area of the IOL. Regarding the design of the IOL having a posterior surface with a smaller radius of curvature, the present invention adopts the higher order aspherical surface design to correct the spherical aberration of the lens and other higher order aberration in the case of a large aperture and disalignment, and improve the imaging quality of the IOL.

(II.2) Toric Surface Design of the Effective Optical Area of the IOL

To correct the refractive power and meanwhile correct the cornea astigmatism after removal of the lens from a cataract patient with astigmatism and thereby further improve visual quality, the effective optical area anterior surface or posterior surface of the obviously rearwardly convex posterior chamber IOL of the present invention may adopt a toric surface design.

Astigmatism property, astigmatism degree and axial position of an astigmatic eye is jointly decided by cornea astigmatism and lens astigmatism. Regarding a cataract patient, after the natural lens is removed, the surface shape defect of the cornea is a main cause for astigmatism. Astigmatism is a vector and can be jointly expressed by magnitude and angle. Briefly speaking, the cornea with astigmatism may be understood as a sum of refractive power of a spherical lens and a cylindrical lens, or as a toric surface with inconsistent diopters in the horizontal direction and vertical direction.

The cause for forming cornea astigmatism may be directed to the cornea as a kind of Toric surface. A mode by which the IOL corrects the cornea astigmatism is to design the IOL as the Toric surface and allow a maximum refractive power axis to coincide with a minimum refractive power axis of the cornea.

To correct pure astigmatism (not including diopter), a cylindrical lens may be used in a way that the refractive power of the cylindrical lens is equal to the magnitude of the cornea astigmatism and opposite in direction. In a cataract surgery in which a lens is implanted, the diopter of the lens needs to be combined with correction of astigmatism so that both the refractive power and the cornea astigmatism can be corrected.

Therefore, the Toric IOL design has the following key points: the first is to perform a basic refractive power design, namely, to satisfy the human eye's requirements for refraction; the second is, on the basis of the basic refractive power design, to use Toric surface shape to additionally provide cylinder power in a certain direction to allow it equal to the magnitude of an additional cylinder power of the cornea and opposite in direction.

Steps for designing the Toric IOL according to the present invention include: designing a basic surface shape of the Toric IOL to satisfy the human eye's requirement for correction of the total refractive power. As far as the present invention is concerned, the IOL needs to reach a refraction range of 5.0D-36.0D in the human eye. Then, there comes to a step of building astigmatism-accompanied cornea and human eye model. Finally, there is a step of additionally providing cylinder power on the basic surface shape of the Toric IOL and correcting cornea astigmatism. As for the present invention, the cylindrical lens degree may be additionally provided by using the surface shape of the toric surface for the effective optical area anterior surface or effective optical area posterior surface.

The Toric surface of the Toric IOL has an axial marker which indicates a minimum refractive power direction of the IOL, and the axial marker needs to be made coincide with a direction with a maximum human eye cornea astigmatism refractive power during a surgical procedure. Studies show that when the axial direction of the Toric IOL rotates more than 5° relative to the axial position of the human eye cornea, the Toric IOL will lose the function to correct astigmatism. Further improving the optical performance of the implanted IOL and meanwhile facilitating the surgeon's mastery of the axial position of the IOL during implantation are factors to be considered in the surface shape design of the effective optical area of the astigmatism-correcting IOL according to the present invention. Therefore, those skilled I the art appreciate that the Toric surface and an ideal position of the axial marker thereof should be located at the IOL anterior surface (in the direction of an anterior chamber).

Most cataract patients with astigmatism have an astigmatic cylinder power in a range of 0.5D-2.5D (data source: ALCON Toric IOL product manual). Therefore, the Toric IOL of the present invention should consider the cylinder power mainly in the range of 0.5D-2.5D upon designing.

With reference to FIG. 18, an anterior surface of the effective optical area of the obviously rearwardly convex posterior chamber IOL according to an embodiment of the present invention comprises: an optic consisting of an effective optical area and an effective optical area edge; at least two haptics connected to the optic. The anterior surface of the effective optical area is a convex toric surface which is formed by superposing a basic spherical surface with a radius of curvature in a range of 7.1 mm-84.0 mm with a deviation quantity relative to the basic spherical surface, and a radius of curvature of the posterior surface of the effective optical area is in a range of 6.6 mm-80.0 mm. A two-dimensional coordinate system is established with an effective optical area anterior surface apex in the posterior chamber IOL as an original point, a longitudinal coordinate axis Y of the coordinate system is tangential with the effective optical area anterior surface and passes through the effective optical area anterior surface apex O; a horizontal coordinate axis Z of the coordinate system is parallel to an ocular axis direction D-D' and is at an angle of 90 degrees relative to the longitudinal coordinate axis Y and passes through the effective optical area anterior surface apex O. A curve of the toric surface on the two-dimensional coordinate system plane YZ satisfies the following expression:

$$Z(y) = \frac{cy^2}{1+\sqrt{1-(1+k)c^2y^2}} + \sum_{i=m}^{n} A_{2i} \cdot y^{2i} \quad (5)$$

Wherein $Z(y)$ is an expression of the curve of the toric surface of the IOL effective optical area on the YZ plane, c is a reciprocal of a radius of curvature of the surface of the basic spherical surface of the effective optical area, y is a vertical distance of any point on the curve from the horizontal coordinate axis Z, $A_{2i}$ is a higher-order term coefficient of the aspherical surface, and m, n are both an integer greater than or equal to 1 and Points on the convex toric surface are obtained in a way that the curve rotates about a straight line d-d' parallel to the longitudinal coordinate axis Y one round with a certain anterior surface rotation radius R.

Characteristics of the toric surface are as follows: the magnitudes of the refractive power in the horizontal direction and vertical direction are different, the refractive power in the vertical direction depends on a radius of curvature of a rotation curve, the refractive power in the horizontal direction depends on the anterior surface rotation radius around which the curve rotates, and the refractive power between the horizontal direction and vertical direction depends on the surface shape formed by rotation of the curve. A refractive power distribution effect of the toric surface is equivalent to the combination of the basic spherical surface and the cylindrical surface.

Table 4 below lists a correspondence relationship between additional cylinder power and a correctable cornea cylinder power of a Toric IOL according to another embodiment of the present invention.

TABLE 4

| Lens cylinder powers | 0.5D | 1.00D | 1.50D | 2.25D | 3.00D | 4.00D | 4.50D | 5.0D |
|---|---|---|---|---|---|---|---|---|
| Cornea cylinder powers | 0.39D | 0.70D | 1.02D | 1.49D | 1.97D | 2.61D | 2.93D | 3.25D |

Table 5 lists a radius of curvature r of an anterior surface standard YZ curve, anterior surface rotation radius R and a radius of curvature of a posterior surface corresponding to different cylinder power in a rearwardly convex Toric IOL with different materials and different degrees.

TABLE 5

| Refractive index and material property | Diopter (D) | Radius of curvature r (mm) of a basic curve of an anterior surface on YZ plane | Radius of curvature (mm) of posterior surface | cylinder power 0.5D; anterior surface rotation radius R (mm) | cylinder power 1.0D; anterior surface rotation radius R (mm) | cylinder power 1.5D; anterior surface rotation radius R (mm) | cylinder power 2.25D; anterior surface rotation radius R (mm) | cylinder power 3.0D; anterior surface rotation radius R (mm) | cylinder power 4.0D; anterior surface rotation radius R (mm) | cylinder power 4.5D; anterior surface rotation radius R (mm) | cylinder power 5.0D; anterior surface rotation radius R (mm) |
|---|---|---|---|---|---|---|---|---|---|---|---|
| 1.46 silicone or hydrogel | 5.0 | 48.600 | 48.00 | 40.64 | 34.92 | 30.61 | 25.83 | 22.34 | 18.93 | 17.59 | 16.42 |
| | 6.0 | 48.500 | 35.00 | 40.57 | 34.86 | 30.57 | 25.80 | 22.32 | 18.91 | 17.57 | 16.41 |
| | 9.0 | 26.500 | 13.00 | 23.94 | 21.83 | 20.07 | 17.90 | 16.15 | 14.29 | 13.51 | 12.81 |
| | 15.0 | 44.500 | 10.00 | 37.73 | 32.75 | 28.93 | 24.62 | 21.43 | 18.27 | 17.02 | 15.92 |
| | 20.0 | 25.600 | 8.00 | 23.20 | 21.22 | 19.55 | 17.48 | 15.81 | 14.02 | 13.27 | 12.60 |
| | 26.5 | 12.000 | 7.50 | 11.45 | 10.94 | 10.48 | 9.85 | 9.30 | 8.65 | 8.36 | 8.09 |
| | 30.0 | 9.200 | 7.30 | 8.87 | 8.56 | 8.28 | 7.88 | 7.53 | 7.09 | 6.90 | 6.71 |
| | 36.0 | 7.100 | 6.60 | 6.90 | 6.72 | 6.54 | 6.29 | 6.06 | 5.78 | 5.65 | 5.52 |
| 1.47 hydrophobic acrylate | 5.0 | 52.500 | 52.00 | 43.90 | 37.72 | 33.07 | 27.90 | 24.13 | 20.45 | 19.00 | 17.74 |
| | 6.0 | 59.000 | 35.00 | 48.35 | 40.96 | 35.53 | 29.64 | 25.42 | 21.37 | 19.79 | 18.43 |
| | 9.0 | 25.500 | 15.00 | 23.28 | 21.42 | 19.84 | 17.85 | 16.23 | 14.48 | 13.74 | 13.07 |
| | 15.0 | 45.500 | 11.00 | 38.90 | 33.97 | 30.15 | 25.79 | 22.54 | 19.29 | 18.00 | 16.87 |
| | 20.0 | 28.700 | 8.50 | 25.92 | 23.64 | 21.72 | 19.37 | 17.47 | 15.46 | 14.61 | 13.86 |
| | 26.5 | 17.000 | 7.00 | 15.99 | 15.09 | 14.28 | 13.22 | 12.31 | 11.28 | 10.82 | 10.40 |
| | 30.0 | 11.000 | 7.30 | 10.57 | 10.17 | 9.79 | 9.29 | 8.83 | 8.28 | 8.03 | 7.80 |
| | 36.0 | 7.800 | 7.00 | 7.58 | 7.37 | 7.17 | 6.90 | 6.64 | 6.33 | 6.18 | 6.04 |
| 1.48 hydrophobic acrylate | 5.0 | 55.100 | 55.00 | 46.09 | 39.62 | 34.74 | 29.32 | 25.36 | 21.50 | 19.97 | 18.65 |
| | 6.0 | 47.138 | 45.50 | 40.39 | 35.33 | 31.39 | 26.90 | 23.53 | 20.17 | 18.82 | 17.64 |
| | 9.0 | 74.026 | 19.50 | 58.63 | 48.54 | 41.41 | 33.94 | 28.75 | 23.88 | 22.01 | 20.42 |
| | 15.0 | 55.743 | 11.10 | 46.54 | 39.95 | 34.99 | 29.50 | 25.50 | 21.59 | 20.06 | 18.73 |

TABLE 5-continued

| Refractive index and material property | Diopter (D) | Radius of curvaturer (mm) of a basic curve of an anterior surface on YZ plane | Radius of curvature (mm) of posterior surface | cylinder power 0.5D; anterior surface rotation radius R (mm) | cylinder power 1.0D; anterior surface rotation radius R (mm) | cylinder power 1.5D; anterior surface rotation radius R (mm) | cylinder power 2.25D; anterior surface rotation radius R (mm) | cylinder power 3.0D; anterior surface rotation radius R (mm) | cylinder power 4.0D; anterior surface rotation radius R (mm) | cylinder power 4.5D; anterior surface rotation radius R (mm) | cylinder power 5.0D; anterior surface rotation radius R (mm) |
|---|---|---|---|---|---|---|---|---|---|---|---|
| | 20.0 | 18.459 | 11.10 | 17.32 | 16.32 | 15.43 | 14.26 | 13.25 | 12.11 | 11.62 | 11.16 |
| | 26.5 | 14.708 | 8.10 | 13.98 | 13.32 | 12.72 | 11.91 | 11.20 | 10.38 | 10.01 | 9.67 |
| | 30.0 | 10.688 | 8.10 | 10.30 | 9.94 | 9.60 | 9.13 | 8.71 | 8.20 | 7.97 | 7.75 |
| | 36.0 | 8.000 | 7.50 | 7.78 | 7.57 | 7.37 | 7.09 | 6.84 | 6.52 | 6.37 | 6.23 |
| 1.49 polymethyl methacrylate (PMMA) | 5.0 | 60.000 | 59.50 | 50.22 | 43.18 | 37.87 | 31.97 | 27.66 | 23.45 | 21.79 | 20.35 |
| | 6.0 | 56.000 | 45.50 | 47.38 | 41.07 | 36.24 | 30.80 | 26.78 | 22.81 | 21.24 | 19.87 |
| | 9.0 | 30.000 | 17.00 | 27.34 | 25.11 | 23.22 | 20.86 | 18.93 | 16.86 | 15.99 | 15.20 |
| | 15.0 | 44.500 | 13.10 | 38.88 | 34.52 | 31.04 | 26.97 | 23.84 | 20.64 | 19.35 | 18.20 |
| | 20.0 | 44.700 | 9.00 | 39.03 | 34.64 | 31.14 | 27.04 | 23.89 | 20.68 | 19.38 | 18.24 |
| | 26.5 | 29.500 | 7.00 | 26.92 | 24.76 | 22.92 | 20.61 | 18.73 | 16.70 | 15.84 | 15.07 |
| | 30.0 | 17.200 | 7.00 | 16.29 | 15.47 | 14.73 | 13.75 | 12.88 | 11.89 | 11.45 | 11.04 |
| | 36.0 | 10.900 | 6.80 | 10.53 | 10.18 | 9.85 | 9.40 | 8.99 | 8.49 | 8.27 | 8.05 |
| 1.51 hydrophobic acrylate | 5.0 | 67.000 | 66.00 | 56.18 | 48.37 | 42.47 | 35.90 | 31.09 | 26.38 | 24.52 | 22.90 |
| | 6.0 | 74.000 | 45.50 | 61.02 | 51.92 | 45.18 | 37.81 | 32.52 | 27.40 | 25.40 | 23.67 |
| | 9.0 | 65.500 | 14.90 | 55.12 | 47.59 | 41.86 | 35.46 | 30.76 | 26.14 | 24.31 | 22.73 |
| | 15.0 | 44.500 | 15.30 | 39.45 | 35.44 | 32.16 | 28.25 | 25.18 | 22.00 | 20.69 | 19.53 |
| | 20.0 | 55.500 | 9.90 | 47.87 | 42.08 | 37.54 | 32.31 | 28.36 | 24.39 | 22.79 | 21.39 |
| | 26.5 | 53.500 | 7.20 | 46.37 | 40.92 | 36.61 | 31.62 | 27.83 | 23.99 | 22.44 | 21.08 |
| | 30.0 | 27.500 | 7.00 | 25.49 | 23.75 | 22.23 | 20.29 | 18.65 | 16.85 | 16.07 | 15.36 |
| | 36.0 | 14.400 | 70.00 | 13.83 | 13.30 | 12.81 | 12.14 | 11.54 | 10.82 | 10.49 | 10.19 |
| 1.52 hydrophobic acrylate | 5.0 | 71.000 | 50.00 | 59.52 | 51.23 | 44.97 | 38.00 | 32.91 | 27.91 | 25.95 | 24.24 |
| | 6.0 | 73.000 | 16.60 | 60.92 | 52.26 | 45.76 | 38.57 | 33.33 | 28.22 | 26.21 | 24.47 |
| | 9.0 | 55.000 | 16.50 | 47.85 | 42.34 | 37.97 | 32.88 | 29.00 | 25.05 | 23.45 | 22.05 |
| | 15.0 | 44.500 | 10.60 | 39.70 | 35.83 | 32.65 | 28.82 | 25.79 | 22.62 | 21.31 | 20.14 |
| | 20.0 | 55.500 | 7.60 | 48.23 | 42.64 | 38.21 | 33.06 | 29.14 | 25.15 | 23.54 | 22.13 |
| | 26.5 | 55.500 | 7.00 | 48.23 | 42.64 | 38.21 | 33.06 | 29.14 | 25.15 | 23.54 | 22.13 |
| | 30.0 | 37.000 | 7.00 | 33.62 | 30.81 | 28.43 | 25.47 | 23.08 | 20.51 | 19.42 | 18.45 |
| | 36.0 | 17.000 | 70.00 | 16.25 | 15.56 | 14.93 | 14.07 | 13.31 | 12.41 | 12.01 | 11.63 |
| 1.55 hydrophobic acrylate | 5.0 | 81.000 | 80.00 | 68.11 | 58.76 | 51.67 | 43.75 | 37.93 | 37.93 | 29.96 | 28.00 |
| | 6.0 | 84.000 | 57.00 | 70.22 | 60.32 | 52.87 | 44.61 | 38.58 | 38.58 | 30.36 | 28.35 |
| | 9.0 | 58.000 | 20.00 | 51.08 | 45.63 | 41.24 | 36.03 | 31.99 | 31.99 | 26.13 | 24.63 |
| | 15.0 | 44.500 | 20.30 | 40.31 | 36.84 | 33.92 | 30.32 | 27.40 | 27.40 | 22.99 | 21.82 |
| | 20.0 | 55.000 | 12.70 | 48.74 | 43.75 | 39.70 | 34.85 | 31.06 | 31.06 | 25.50 | 24.07 |
| | 26.5 | 55.500 | 9.00 | 49.13 | 44.07 | 39.96 | 35.05 | 31.21 | 31.21 | 25.61 | 24.16 |
| | 30.0 | 53.000 | 7.80 | 47.16 | 42.48 | 38.64 | 34.03 | 30.41 | 30.41 | 25.07 | 23.68 |
| | 36.0 | 30.800 | 7.00 | 28.73 | 26.92 | 25.33 | 23.27 | 21.51 | 21.51 | 18.69 | 17.91 |

The following can be seen from data of examples in Table 5:

Regarding the obviously rearwardly convex posterior chamber IOL made of silicone or hydrogel with a refractive index 1.46 and having the effective optical area anterior surface adopting the toric surface design, the radius of curvature of the basic curve of the effective optical area anterior surface on the YZ plane is in a range of 7.1 mm-48.6 mm; when the additional cylinder power of the toric surface is in a range of 0.5-5.0D, the anterior surface rotation radius is in a range of 5.52-40.64 mm. To better achieve the above advantageous effect of the present invention, the radius of curvature of the basic curve of the effective optical area anterior surface on the YZ plane is preferably in a range of 9.2 mm-44.5 mm; when the additional cylinder power of the toric surface is in a range of 1.0-4.0D, the anterior surface rotation radius is in a range of 7.09-32.75 mm. More preferably, the radius of curvature of the basic curve of the effective optical area anterior surface on the YZ plane is about 12.0 mm; when the additional cylinder power of the toric surface is 2.25D, the anterior surface rotation radius is about 9.85 mm.

Regarding the obviously rearwardly convex posterior chamber IOL made of hydrophobic acrylate with a refractive index 1.47 and having the effective optical area anterior surface adopting the toric surface design, the radius of curvature of the basic curve of the effective optical area anterior surface on the YZ plane is in a range of 7.8 mm-59.0 mm; when the additional cylinder power of the toric surface is in a range of 0.5-5.0D, the anterior surface rotation radius is in a range of 6.04-48.35 mm. To better achieve the above advantageous effect of the present invention, the radius of curvature of the basic curve of the effective optical area anterior surface on the YZ plane is preferably in a range of 11.0 mm-45.5 mm; when the additional cylinder power of the toric surface is in a range of 1.0-4.0D, the anterior surface rotation radius is in a range of 8.28-33.97 mm. More preferably, the radius of curvature of the basic curve of the effective optical area anterior surface on the YZ plane is about 17.0 mm; when the additional cylinder power of the toric surface is 2.25D, the anterior surface rotation radius is about 13.22 mm.

Regarding the obviously rearwardly convex posterior chamber IOL made of hydrophobic acrylate with a refractive index 1.48 and having the effective optical area anterior surface adopting the toric surface design, the radius of curvature of the basic curve of the effective optical area anterior surface on the YZ plane is in a range of 8.0 mm-74.0 mm; when the additional cylinder power of the toric surface is in a range of 0.5-5.0D, the anterior surface rotation radius is in a range of 6.23-58.63 mm. To better achieve the above advantageous effect of the present invention, the radius of curvature of the basic curve of the effective optical area anterior surface on the YZ plane is preferably in a range of 10.69 mm-55.74 mm; when the additional cylinder power of the toric surface is in a range of 1.0-4.0D, the anterior surface rotation radius is in a range of 8.2-39.95 mm. More preferably, the radius of curvature of the basic curve of the effective optical area anterior surface on the YZ plane is about 14.71 mm; when the additional cylinder power of the toric surface is 2.25D, the anterior surface rotation radius is about 11.91 mm.

Regarding the obviously rearwardly convex posterior chamber IOL made of polymethyl methacrylate (PMMA) with a refractive index 1.49 and having the effective optical area anterior surface adopting the toric surface design, the radius of curvature of the basic curve of the effective optical area anterior surface on the YZ plane is in a range of 10.9 mm-60.0 mm; when the additional cylinder power of the toric surface is in a range of 0.5-5.0D, the anterior surface rotation radius is in a range of 8.05-59.50 mm. To better achieve the above advantageous effect of the present invention, the radius of curvature of the basic curve of the effective optical area anterior surface on the YZ plane is preferably in a range of 17.2 mm-44.5 mm; when the additional cylinder power of the toric surface is in a range of 1.0-4.0D, the anterior surface rotation radius is in a range of 11.89-34.64 mm. More preferably, the radius of curvature of the basic curve of the effective optical area anterior surface on the YZ plane is about 29.5 mm; when the additional cylinder power of the toric surface is 2.25D, the anterior surface rotation radius is about 20.61 mm.

Regarding the obviously rearwardly convex posterior chamber IOL made of hydrophobic acrylate with a refractive index 1.51 and having the effective optical area anterior surface adopting the toric surface design, the radius of curvature of the basic curve of the effective optical area anterior surface on the YZ plane is in a range of 14.4 mm-74.0 mm; when the additional cylinder power of the toric surface is in a range of 0.5-5.0D, the anterior surface rotation radius is in a range of 10.19-61.02 mm. To better achieve the above advantageous effect of the present invention, the radius of curvature of the basic curve of the effective optical area anterior surface on the YZ plane is preferably in a range of 27.5 mm-55.5 mm; when the additional cylinder power of the toric surface is in a range of 1.0-4.0D, the anterior surface rotation radius is in a range of 16.85-42.08 mm. More preferably, the radius of curvature of the basic curve of the effective optical area anterior surface on the YZ plane is about 53.5 mm; when the additional cylinder power of the toric surface is 2.25D, the anterior surface rotation radius is about 31.62 mm.

Regarding the obviously rearwardly convex posterior chamber IOL made of hydrophobic acrylate with a refractive index 1.52 and having the effective optical area anterior surface adopting the toric surface design, the radius of curvature of the basic curve of the effective optical area anterior surface on the YZ plane is in a range of 17.0 mm-73.0 mm; when the additional cylinder power of the toric surface is in a range of 0.5-5.0D, the anterior surface rotation radius is in a range of 11.63-60.92 mm. To better achieve the above advantageous effect of the present invention, the radius of curvature of the basic curve of the effective optical area anterior surface on the YZ plane is preferably in a range of 37.0 mm-44.5 mm; when the additional cylinder power of the toric surface is in a range of 1.0D-4.0D, the anterior surface rotation radius is in a range of 20.51-42.64 mm. More preferably, the radius of curvature of the basic curve of the effective optical area anterior surface on the YZ plane is about 55.5 mm; when the additional cylinder power of the toric surface is 2.25D, the anterior surface rotation radius is about 33.06 mm.

Regarding the obviously rearwardly convex posterior chamber IOL made of hydrophobic acrylate with a refractive index 1.55 and having the effective optical area anterior surface adopting the toric surface design, the radius of curvature of the basic curve of the effective optical area anterior surface on the YZ plane is in a range of 30.8 mm-84.0 mm; when the additional cylinder power of the toric surface is in a range of 0.5-5.0D, the anterior surface rotation radius is in a range of 17.91-70.22 mm. To better achieve the above advantageous effect of the present invention, the radius of curvature of the basic curve of the effective optical area anterior surface on the YZ plane is preferably in a range of 44.5 mm-55.5 mm; when the additional cylinder power of the toric surface is in a range of 1.0D-4.0D, the anterior surface rotation radius is in a range of 30.41-44.07 mm. More preferably, the radius of curvature of the basic curve of the effective optical area anterior surface on the YZ plane is about 55.5 mm; when the additional cylinder power of the toric surface is 2.25D, the anterior surface rotation radius is about 35.05 mm.

Certainly, those skilled in the art may appreciate that the posterior surface of the effective optical area of the Toric IOL of the present invention may adopt a spherical surface design or other designs such as adding a higher order aspherical surface design on the basic spherical surface.

As compared with ordinary aspherical surface IOL in the prior art, the anterior surface of the effective optical area of the Toric IOL of the present invention adopts a toric surface design and thereby improves the visual quality of the cataract patient with astigmatism, as shown in FIGS. 19A, 19B, 20A and 20B.

FIG. 19A and FIG. 19B are respectively a point spread function contrast diagram after an ordinary aspherical surface intraocular lens and Toric intraocular lens of the present invention are respectively implanted into a human eye with corneal astigmatism obtained through simulation by adopting ZEMAX, wherein the human eye model has 2.9D corneal astigmatism. It can be seen after comparison of FIG. 19A and FIG. 19B that the human eye in which the ordinary aspherical surface IOL is implanted suffers from astigmatism, the point spread function is in a straight line shape, the imaging situation in one direction (longitudinal direction) is excellent while and the higher order aberration in another direction (horizontal direction) is extremely great. After implantation of Toric IOL, the point spread function is in a dot shape. Although partial astigmatism still exists the human eye, it is already corrected substantially (please note the two figures are in different scales).

FIG. 20A and FIG. 20B are respectively an MTF contrast diagram after an ordinary aspherical intraocular lens and Toric intraocular lens of the present invention are respectively implanted into a human eye with corneal astigmatism obtained through simulation by adopting ZEMAX, wherein the human eye model has 2.9D corneal astigmatism. It can be seen after comparison of FIG. 20A and FIG. 20B that for the human eye in which the ordinary aspherical surface IOL, MTF reaches a diffraction extremity and images are formed very well in one direction, while MTF falls to an extremely low level in another direction. With the Toric IOL of the present invention being implanted, MTF in two directions both reaches a level approximate to the diffraction extremity.

As can be seen from the above figures, the obviously rearwardly convex Toric IOL with the effective optical area anterior surface adopting the toric surface according to an embodiment of the present invention correct the refractive power as well as the corneal astigmatism at the same time, thereby improving the visual quality of the cataract patient with the astigmatism.

In another toric surface design, in order to eliminate or reduce the higher order aberration (including the spherical aberration and comatic aberration) of the IOL product in the prior art and thereby improve the imaging quality, the anterior surface of the effective optical area of the posterior chamber IOL of the present invention adopts the toric surface design and the posterior surface of the effective optical area of the posterior chamber IOL of the present invention adopts a higher order aspherical surface design.

The following Table 6 lists surface shape parameters of one preferred embodiment of the posterior chamber IOL of the present invention adopting the toric surface design and a comparative example in the prior art. Both the preferred embodiment of the present invention and the comparative example of the prior art are made of hydrophobic acrylate and this material is available from Eyebright Medical Technology (Beijing) Co., Ltd. The material of the posterior chamber IOL has a refractive index 1.48 (20□). The refractive index of the material is proper, and can effectively reduce occurrence rate of dazzling and ghosting. The posterior chamber IOL according to the following preferred embodiment of the present invention all can reach 20.0D diopter (the additional cylinder power is 2.5D). In Table 6, Ra is a radius of curvature of the IOL anterior surface (the measure unit is millimeter), Rp is a radius of curvature of the IOL posterior surface (the measure unit is millimeter), the value of the radius of curvature is a positive number, which indicates that the surface is outwardly convex relative to a longitudinal central plane of the effective optical area of the IOL, and A4, A6, A8, A10 are coefficient values (see the preceding text of the aspherical surface of the IOL.

TABLE 6

|  | Ra | Rp | A4 | A6 | A8 | A10 |
|---|---|---|---|---|---|---|
| Preferred embodiment | 18.46 | 11.1 | 6.46E−004 | 9.86E−005 | −2.19E−005 | 1.12E−006 |
| Comparative example | 18.46 | 11.1 | −1.85E−004 | −2.14E−004 | 3.27E−005 | −1.47E−006 |

It can be seen from Table 6 that the preferred embodiment of the posterior chamber IOL of the present invention and the comparative example in the prior art both have an obviously rearwardly convex surface shape design for the posterior surface of the effective optical area.

It can be further seen from Table 6 that in the preferred embodiment of the posterior chamber IOL of the present invention, the toric surface is at the anterior surface of the effective optical area of the IOL, and all aspherical surfaces are located at the posterior surface of the effective optical area of the IOL; in the comparative example, both the toric surface and the aspherical surface are located at the anterior surface of the effective optical area of the IOL.

FIG. 23 illustratively shows a positional relationship between an intraocular lens axial direction and a maximum refractive power direction of the human cornea when the Toric intraocular lens is implanted into a human eye. When a difference of over 5° is generated between the IOL axial direction and a human eye cornea 11 when the IOL is implanted into the human eye, and the patient's eyesight will be affected seriously. Therefore, an easily recognizable and clear direction marker on the Toric surface is an objective requirement in the surgical procedure for the Toric IOL design. It can be seen that in the preferred embodiment of the posterior chamber IOL of the present invention, it is very favorable that the toric surface is disposed at the anterior surface of the effective optical area of the IOL.

FIG. 24 illustratively shows a MTF contrast diagram of the intraocular lens (preferred embodiment) of the present invention with an aspherical surface and a toric surface being respectively located on both sides and an intraocular lens (comparative example) with the aspherical surface and the toric surface being located on the same side, at a spatial frequency of 0-100 lp/mm in a human eye model with astigmatism and a pupil diameter 3.0 mm.

In FIG. 24, the solid line is MTF curve of an IOL (the preferred embodiment) with the aspherical surface and the Toric surface being respectively located on both sides of the lens at a spatial frequency of 0-100 lp/mm in a human eye model with astigmatism and a pupil diameter 3.0 mm; the dotted line is MTF curve of an IOL (the comparative example) with the aspherical surface and a Toric surface being located on the same side of the lens at a spatial frequency of 0-100 lp/mm in a human eye model with astigmatism and a pupil diameter 3.0 mm. As can be seen from the figure, the MTF curve of an IOL with the aspherical surface and the Toric surface being respectively located on both sides of the lens is higher than the MTF curve of an IOL with the aspherical surface and the Toric surface being located on the same side of the lens, which indicates that under the same condition (at the same astigmatism human eye model, and the aspherical surface coefficients are all optimized), the optical performance of the IOL with the aspherical surface and the Toric surface being respectively located on both sides of the lens is better than the IOL with the aspherical surface and the Toric surface being located on the same side of the lens.

FIG. 25 illustratively shows a wave front chart of a surface shape design of an astigmatism correction IOL of the present invention at an image surface in a human eye model (a preferred embodiment; with the aspherical surface and the toric surface being respectively located on both sides of the IOL); and FIG. 26 illustrates a wave front chart of a surface shape design (a comparative example) in the prior art in the same human eye model with the aspherical surface and the toric surface being combined on one surface in the prior art.

It can be seen by comparing the wavefront aberrations in FIG. 25 and FIG. 26 that the IOL with the toric surface and the aspherical surface separate has a smaller image surface wavefront astigmatism-like fluctuation in an astigmatic eye, with a wavefront aberration PV value being 0.1060λ, and RMS value being 0.0241λ; the image surface of the design with the toric surface and the aspherical surface being combined on one surface has an apparent astigmatism-like fluctuation, with a wavefront aberration PV value being 0.3331λ, and RMS value being 0.0700λ. Therefore, it is proved that the IOL with the toric surface and the aspherical surface separate has a better astigmatism correction effect for the cornea and a smaller wavefront aberration after correction.

To conclude, as compared with posterior chamber IOL in the prior art, the effective optical area of the posterior chamber IOL of the present invention adopts a design with the posterior surface obviously convex (with a small radius of curvature) and adopts a higher order aspherical surface design or additionally adopts a toric surface design, which reduces the distance between the posterior surface of the effective optical area of the IOL and the posterior capsule, improves stability of a spatial position of the IOL in a capsule bag, gives full play to advantages of the right-angle edge effect of the IOL optical effective area edge, and reduces an incidence rate of posterior capsule opacification (PCO) after implantation of the IOL; since the effective optical area anterior surface is relatively flat, the IOL haptics (particularly with haptics of the one-piece posterior chamber IOL) will not be tightly pressed on the effective optical area anterior surface upon folding, the haptics are more easily unfolded after implantation into the eye and the support haptics are not mutually adhered to the effective optical area, and meanwhile the IOL imaging quality can be improved and/or the visual quality of the astigmatism sufferer is enhanced.

The embodiments described above are only exemplary and not restrictive. Therefore, without departing from the inventive concept disclosed in the description, those skilled in the art may modify or change the above embodiments. Hence, the protection scope of the present invention is only defined by the appended claims.

The invention claimed is:

1. A posterior chamber intraocular lens (IOL) comprising:
an optic consisting of an effective optical area and an effective optical area edge disposed around the effective optical area;
at least two haptics symmetrically connected to the optic around a circumferential direction of the optic, the at least two haptics selected from the group consisting of L-shaped haptics and C-shaped haptics,
wherein:
an anterior optical surface of the effective optical area is a convex surface, and a basic spherical surface thereof has a radius of curvature in a range of 14.4 mm to 74.0 mm,
a posterior optical surface of the effective optical area is a convex aspherical surface, and a basic spherical surface thereof has a radius of curvature in a range of 7.2 mm to 15.3 mm, and the radius of curvature of the basic spherical surface of the posterior optical surface of the effective optical area is smaller than the radius of curvature of the anterior optical surface of the effective optical area,
wherein the radius of curvature of the basic spherical surface of the posterior optical surface of the effective optical area is 17.8%-60.0% of the radius of curvature of the anterior optical surface of the effective optical area,
wherein the posterior chamber intraocular lens comprises hydrophobic acrylate having a refractive index of 1.47-1.55,
wherein roots of the haptics are directly connected to the effective optical area edge of the optic,
wherein the effective optical area edge further comprises a sharp bend dimensioned and configured to press tightly against the posterior capsule membrane of the eye,
wherein the convex aspherical surface of the posterior optical surface comprises a high order aspherical surface design in order to correct spherical aberration and high order aberrations, and to further improve the imaging quality of the basic spherical surface, and
wherein substantially the entirety of the posterior optical surface of the effective optical area is dimensioned and configured to be in direct close contact with the posterior capsule membrane of the eye to improve the stability of a spatial position of the IOL in the capsule bag and also to reduce incidence rate of posterior capsule opacification (PCO) after implantation of the IOL into the human eye.

2. The posterior chamber IOL according to claim 1, wherein the radius of curvature of the basic spherical surface of the posterior optical surface of the effective optical area is 20.0%-45.6% of the radius of curvature of the anterior optical surface of the effective optical area.

3. The posterior chamber IOL according to claim 1, wherein a longitudinal center line of the haptic roots is at a haptic angle in a range of 0°-7° relative to a longitudinal center line of the optic.

4. The posterior chamber IOL according to claim 1, wherein the surface shape of an the anterior optical surface of the effective optical area comprises one of spherical surface, aspherical surface, toric surface, multi-focal surface of multi-area refraction design and multi-focal surface of multi-area diffraction design.

* * * * *